United States Patent
Quake et al.

(10) Patent No.: US 10,988,804 B2
(45) Date of Patent: **\*Apr. 27, 2021**

(54) NUCLEIC ACID SEQUENCING APPARATUS FOR MONITORING STATUS OF A TRANSPLANT RECIPIENT

(71) Applicant: The Board of Trustees of the Leland Stanford Junior University, Stanford, CA (US)

(72) Inventors: Stephen R. Quake, Stanford, CA (US); Thomas M. Snyder, Palo Alto, CA (US); Hannah Valantine, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/361,741

(22) Filed: Mar. 22, 2019

(65) Prior Publication Data

US 2019/0211375 A1    Jul. 11, 2019

Related U.S. Application Data

(63) Continuation of application No. 15/788,549, filed on Oct. 19, 2017, which is a continuation of application No. 14/188,455, filed on Feb. 24, 2014, now Pat. No. 9,845,497, which is a continuation of application No. 13/508,318, filed as application No. PCT/US2010/055604 on Nov. 5, 2010, now Pat. No. 8,703,652.

(60) Provisional application No. 61/280,674, filed on Nov. 6, 2009.

(51) Int. Cl.
| | | |
|---|---|---|
| C12Q 1/686 | (2018.01) | |
| C12Q 1/6869 | (2018.01) | |
| C12Q 1/6837 | (2018.01) | |
| G16B 20/00 | (2019.01) | |
| C12Q 1/6883 | (2018.01) | |

(52) U.S. Cl.
CPC .......... *C12Q 1/686* (2013.01); *C12Q 1/6837* (2013.01); *C12Q 1/6869* (2013.01); *G16B 20/00* (2019.02); *C12Q 1/6883* (2013.01); *C12Q 2600/106* (2013.01)

(58) Field of Classification Search
None
See application file for complete search history.

(56) References Cited

U.S. PATENT DOCUMENTS

| | | |
|---|---|---|
| 4,466,467 A | 8/1984 | Tolliver |
| 5,403,833 A | 4/1995 | Caine et al. |
| 5,432,054 A | 7/1995 | Saunders et al. |
| 5,733,729 A | 3/1998 | Lipshutz et al. |
| 5,858,412 A | 1/1999 | Stankforth et al. |
| 6,258,540 B1 | 7/2001 | Lo et al. |
| 6,355,431 B1 | 3/2002 | Chee et al. |
| 6,396,995 B1 | 5/2002 | Stuelpnagel et al. |
| 6,429,027 B1 | 8/2002 | Chee et al. |
| 6,492,144 B1 | 12/2002 | Umansky et al. |
| 6,505,125 B1 | 1/2003 | Ho et al. |
| 6,544,732 B1 | 4/2003 | Chee et al. |
| 6,620,584 B1 | 9/2003 | Chee et al. |
| 6,663,832 B2 | 12/2003 | Lebl et al. |
| 6,770,441 B2 | 8/2004 | Dickinson et al. |
| 6,787,308 B2 | 9/2004 | Balasubramanian et al. |
| 6,812,005 B2 | 11/2004 | Fan et al. |
| 6,833,246 B2 | 12/2004 | Balasubramanian et al. |
| 6,846,460 B1 | 1/2005 | Lebl et al. |
| 6,858,394 B1 | 2/2005 | Chee et al. |
| 6,890,741 B2 | 5/2005 | Fan et al. |
| 6,890,764 B2 | 5/2005 | Chee et al. |
| 6,897,023 B2 | 5/2005 | Fu et al. |
| 6,913,884 B2 | 7/2005 | Stuelpnagel et al. |
| 6,942,968 B1 | 9/2005 | Dickinson et al. |
| 6,969,488 B2 | 11/2005 | Bridgham et al. |
| 6,998,274 B2 | 2/2006 | Chee et al. |
| 7,025,935 B2 | 4/2006 | Jones et al. |
| 7,033,754 B2 | 4/2006 | Chee et al. |
| 7,035,740 B2 | 4/2006 | Kermani et al. |
| 7,040,959 B1 | 5/2006 | Panuska et al. |
| RE39,920 E | 11/2007 | Umanski et al. |
| 7,316,897 B2 | 1/2008 | de Saint Julien et al. |
| 7,473,767 B2 | 1/2009 | Dimitrov et al. |
| 7,732,134 B2 | 6/2010 | Kudaravalli et al. |
| 7,829,285 B2 | 11/2010 | Lo et al. |
| 8,703,652 B2 | 4/2014 | Quake et al. |
| 8,999,644 B2 | 4/2015 | Hall et al. |

(Continued)

FOREIGN PATENT DOCUMENTS

| | | |
|---|---|---|
| DE | 10149786 A1 | 7/2003 |
| DE | 10214395 A1 | 10/2003 |

(Continued)

OTHER PUBLICATIONS

Roedder et al. (Genome Medicine 2011, 3:37, pp. 1-12) (Year: 2011).*
Fan et al. (PNAS, 2008, 105(42), 16266-16271) (Year: 2008).*
Zheng et al. (Clinical Chemistry, 1999, 45(10), pp. 1741-1746) (Year: 1999).*
Adams et al., "The genome sequence of *Drosophila melanogaster*",Science. Mar. 24, 2000, pp. 2185-2195, vol. 287, Issue 5461, American Association for the Advancement of Science, Washington, D.C.
Applied Biosystems, "Assays-on-Demand Gene Expressions Products Protocol", ABI Prism 7000 Sequence Detection System, 2003, pp. I-40, Applied Biosystems, Foster City, CA.

(Continued)

*Primary Examiner* — Pablo S Whaley
(74) *Attorney, Agent, or Firm* — Pamela J. Sherwood; Bozicevic, Field & Francis LLP

(57) ABSTRACT

The invention provides methods, devices, compositions and kits for diagnosing or predicting transplant status or outcome in a subject who has received a transplant.

19 Claims, 6 Drawing Sheets

Specification includes a Sequence Listing.

(56) References Cited

U.S. PATENT DOCUMENTS

| | | | |
|---|---|---|---|
| 9,845,497 | B2 | 12/2017 | Quake et al. |
| 2002/0012930 | A1 | 1/2002 | Rothberg et al. |
| 2002/0177141 | A1 | 1/2002 | Rothberg et al. |
| 2002/0187515 | A1 | 1/2002 | Rothberg et al. |
| 2003/0003490 | A1 | 1/2003 | Fan et al. |
| 2003/0022207 | A1 | 1/2003 | Balasubramanian et al. |
| 2003/0044781 | A1 | 3/2003 | Korlach et al. |
| 2003/0058629 | A1 | 3/2003 | Hirai et al. |
| 2003/0064398 | A1 | 4/2003 | Barnes |
| 2003/0100102 | A1 | 5/2003 | Rothberg et al. |
| 2003/0148344 | A1 | 8/2003 | Rothberg et al. |
| 2003/0175773 | A1 | 9/2003 | Chee et al. |
| 2003/0198573 | A1 | 10/2003 | Forood et al. |
| 2004/0106130 | A1 | 6/2004 | Besemer et al. |
| 2004/0137470 | A1 | 7/2004 | Dhallan |
| 2004/0185482 | A1 | 9/2004 | Stuelpnagel et al. |
| 2004/0224353 | A1 | 11/2004 | Fan et al. |
| 2004/0241764 | A1 | 12/2004 | Galili |
| 2004/0248161 | A1 | 12/2004 | Rothberg et al. |
| 2005/0079510 | A1 | 4/2005 | Berka et al. |
| 2005/0100932 | A1 | 5/2005 | Lapidus et al. |
| 2005/0124022 | A1 | 6/2005 | Srinivasan et al. |
| 2005/0164246 | A1 | 7/2005 | Fan et al. |
| 2005/0181394 | A1 | 8/2005 | Steemers et al. |
| 2005/0216207 | A1 | 9/2005 | Kermani |
| 2005/0244870 | A1 | 11/2005 | Chee et al. |
| 2005/0266432 | A1 | 12/2005 | Oliphant et al. |
| 2005/0282185 | A1 | 12/2005 | Yuk-Ming et al. |
| 2006/0012784 | A1 | 1/2006 | Ulmer |
| 2006/0012793 | A1 | 1/2006 | Harris |
| 2006/0019258 | A1 | 1/2006 | Yeakley |
| 2006/0024678 | A1 | 2/2006 | Buzby |
| 2006/0024711 | A1 | 2/2006 | Lapidus et al. |
| 2006/0078909 | A1 | 4/2006 | Srinivasan et al. |
| 2006/0078937 | A1 | 4/2006 | Korlach et al. |
| 2007/0031890 | A1* | 2/2007 | Wohlgemuth ....... C12Q 1/6881 435/7.1 |
| 2007/0037166 | A1 | 2/2007 | Wohlgemuth et al. |
| 2007/0166708 | A1 | 7/2007 | Dimitrov et al. |
| 2007/0202525 | A1 | 8/2007 | Quake et al. |
| 2009/0026082 | A1 | 1/2009 | Rothberg et al. |
| 2009/0029377 | A1 | 1/2009 | Ehrich et al. |
| 2009/0053719 | A1 | 2/2009 | Lo et al. |
| 2009/0081640 | A1 | 3/2009 | Umansky et al. |
| 2009/0170102 | A1 | 7/2009 | Lo et al. |
| 2009/0221620 | A1 | 9/2009 | Luke et al. |
| 2009/0263800 | A1* | 10/2009 | Wohlgemuth ....... C12Q 1/6883 435/6.18 |
| 2010/0233716 | A1 | 9/2010 | Saint-Mezard et al. |
| 2010/0261026 | A1 | 10/2010 | Ferree et al. |
| 2010/0305000 | A1 | 12/2010 | Mathew et al. |
| 2010/0330035 | A1 | 12/2010 | Hildebrandt-Eriksen et al. |
| 2012/0108460 | A1 | 5/2012 | Quake et al. |
| 2012/0115737 | A1 | 5/2012 | Ehrich et al. |
| 2012/0196754 | A1 | 8/2012 | Quake et al. |
| 2012/0295810 | A1 | 11/2012 | Quake et al. |
| 2013/0252835 | A1 | 9/2013 | Koh et al. |
| 2018/0030514 | A1 | 2/2018 | Quake et al. |
| 2018/0371530 | A1 | 12/2018 | Quake et al. |
| 2018/0371531 | A1 | 12/2018 | Quake et al. |

FOREIGN PATENT DOCUMENTS

| | | |
|---|---|---|
| DE | 10356837 A1 | 6/2005 |
| DE | 102004009704 A1 | 9/2005 |
| DE | 102004025744 A1 | 12/2005 |
| DE | 102004025745 A1 | 12/2005 |
| DE | 102004025746 A1 | 12/2005 |
| DE | 102004025694 A1 | 2/2006 |
| DE | 102004025695 A1 | 2/2006 |
| DE | 102004025696 A1 | 2/2006 |
| DE | 60123448 T2 | 8/2007 |
| EP | 1325963 A1 | 7/2003 |
| JP | 2004504014 | 2/2004 |
| JP | 2004504014 A | 2/2004 |
| JP | 2009072060 A | 4/2009 |
| JP | 2018138055 A | 9/2018 |
| WO | 1999/018231 A1 | 4/1999 |
| WO | 2001088196 | 11/2001 |
| WO | 2002/061148 A2 | 8/2002 |
| WO | 2002/088382 A2 | 11/2002 |
| WO | 2003/020968 A2 | 3/2003 |
| WO | 2003/020974 A2 | 3/2003 |
| WO | 2003020968 A3 | 3/2003 |
| WO | 2003/031947 A2 | 4/2003 |
| WO | 02088382 A3 | 8/2003 |
| WO | 03031947 A3 | 12/2003 |
| WO | 2005/044836 A2 | 5/2005 |
| WO | 2005044836 A3 | 7/2007 |
| WO | 2008/056937 A1 | 5/2008 |
| WO | 2008/079374 A2 | 7/2008 |
| WO | 2008084405 A3 | 1/2009 |
| WO | 2009/060035 A1 | 5/2009 |
| WO | 2009/102470 A2 | 8/2009 |
| WO | 2011/057061 A1 | 5/2011 |
| WO | 2011/140433 A2 | 11/2011 |

OTHER PUBLICATIONS

Barnes et al., "Experimental comparison and cross-validation of the Affymetrix andIllumina gene expression analysis platforms", Nucleic Acids Res., Jan. 1, 2005, pp. 5914-5923, vol. 33, Issue 18, Oxford University Press, Oxford, United Kingdom.

Baxter-Lowe et al., "Tracking microchimeric DNA in plasma to diagnose andmanage organ transplant rejection", Clin Chern., Apr. 2006, pp. 559-561, vol. 52, Issue 4, American Association for Clinical Chemistry, Washington, DC.

Bianchi, et al. "Isolation of fetal DNA from nucleated erythrocytes in maternal blood", Proc Natl Acad Sci U SA., May 1, 1990, pp. 3279-3283, vol. 87 No. 9 , PNAS, Washington, DC.

Bibikov et al., "Gene expression profiles in formalin-fixed, paraffin-embeddedtissues obtained with a novel assay for microarray analysis", Clin Chern., Dec. 2004, pp. 2384-2386, vol. 50, Issue 12, American Association for Clinical Chemistry, Washington, DC.

Borrill et al., "The use of short tandem repeat polymorphisms for monitoringchimerism following bone marrow transplantation: a short report", Hematology, Aug. 2008, pp. 210-214, vol. 13, Issue 4, Informa UK Limited, London, United Kingdom.

Ossola, et al., "Circulating bacterial-derived DNA fragments and markers of inflammation in chronic hemodialysis patients", Clin JAm Soc Nephrol, Feb. 2009, pp. 379-385, vol. 4 No. 2 , American Society of Nephrology, Washington, DC.

Bruch, et al., "Trophoblast-like cells sorted from peripheral maternal blood using flow cytometry: a multiparametric Study involving transmission electron microscopy and fetal DNA amplification", Prenat Diagn, Oct. 1991 ,pp. 787-798, vol. 11, Issue 10, John Wiley & Sons, Ltd., Hoboken, NJ.

De La Vega et al., "Assessment of two flexible and compatible SNP genotyping platforms: TaqMan SNP Genotyping Assays and the SNPlex Genotyping System", Mutat Res., Jun. 3, 2005, pp. 111-135, 573(1-2), Elsevier, Amsterdam, Netherlands.

Devlaminck et al., "Circulating Cell-Free DNA Enables Noninvasive Diagnosis of Heart Transplant Rejection", Science Translational Medicine, Jun. 18, 2014, pp. 1-9, vol. 6, Issue 241, American Association for the Advancement of Science, Washington, D.C.

Di et al., "Dynamic model based algorithms for screening and genotyping over 100 KSNPs on oligonucleotide microarrays", Bioinformatics, May 1, 2005), pp. 1958-1963, vol. 21, Issue 9, Oxford University Press, Oxford, United Kingdom.

Diehl et al., "Circulating mutant DNA to assess tumor dynamics", Nat Med., Sep. 2008. pp. 985-990, 14(9), Macmillan Publishers Limited, Basingstoke, United Kingdom.

Diehl et al., "Detection and quantification of mutations in the plasma of patients withcolorectal tumors", Proc Natl Acad Sci USA, Nov. 8, 2005, pp. 16368-16373, vol. 102 No. 45, PNAS, Washington, DC.

(56) References Cited

OTHER PUBLICATIONS

Faham et al., "Mismatch repair detection (MRD): high-throughput scanning for DNA variations", Hum Mol Genet, Aug. 1, 2001, pp. 1657-1664, vol. 10, Issue 16, vol. 10, Issue 16, Oxford University Press, Oxford, United Kingdom.

Fakhrai-Rad et al., "SNP discovery in pooled samples with mismatch repair detection", Genome Res., Jul. 2004, pp. 1404-1412, 14(7), Cold Spring Harbor Laboratory, Huntington, NY.

Fan et al., "Detection of aneuploidy with digital polymerase chain reaction", Anal Chem., Oct. 1, 2007, pp. 7576-7579, 79(19), American Chemical Society, Washington, D.C.

Fan et al., "Noninvasive diagnosis of fetal aneuploidy by shotgun sequencing DNA from maternal blood", Proc Natl Acad Sci USA, Oct. 21, 2008, pp. 16266-16271, vol. 105 No. 42, PNAS, Washington, DC.

Fitzgerald et al., "Intravascular ultrasound imaging of coronary arteries. Is threelayers the norm?", Circulation, Jul. 1, 1992, pp. 154-158, vol. 86, Issue 1, American Heart Association, Inc., Dallas, TX.

Fournie et al., "Plasma DNA as a marker of cancerous cell death. Investigations inpatients suffering from lung cancer and in nude mice bearing human tumours", Cancer Lett., May 8, 1995, pp. 221-227, vol. 91, Issue 2, Elsevier, Amsterdam, Netherlands.

Gadi et al., "Soluble donor DNA concentrations in recipient serum correlate withpancreas-kidney rejection", Clin Chem., Mar. 2006, pp. 379-382, vol. 52, Issue 3, American Association for Clinical Chemistry, Washington, DC.

Giacona et al., "Cell-free DNA in human blood plasma: length measurements in patients with pancreatic cancer and healthy controls", Pancreas, Jul. 1998, pp. 89-97, 17(1), Wolters Kluwer Health, Inc., Philadelphia, PA.

Gonzalez, et al., "Multiple displacement amplification as a prepolymerase chain reaction (pre-PCR) to processDifficult to amplify samples and low copy number sequences from natural environments", Environ Microbial., Jul. 7, 2005, pp. 1024-1028, vol. 7, Issue 7, John Wiley & Sons, Inc., Hoboken, NJ.

Hardenbol et al., "Highly multiplexed molecular inversion probe genotyping: Over 10,000 targeted SNPs genotyped in a single tube assay", Genome Res., Feb. 2005, pp. 269-275,15(2), Cold Spring Harbor Laboratory, Huntington, NY.

Hardenbol et al., "Multiplexed genotyping with sequence-tagged molecularin version probes", Nat Biotechnol., Jun. 2003, p. 673-678, vol. 21, No. 6, Nature Publishing, London, United Kingdom.

Harris et al., "Single-molecule DNA sequencing of a viral genome", Science, Apr. 4, 2008, pp. 106-109, vol. 320, Issue 5872, American Association for the Advancement of Science, Washington, D.C.

Herzenberg, et al., "Fetal cells in the blood of pregnant women: detection and enrichment by fluorescence-Activated cell sorting", Proc Natl Acad Sci U S A, Mar. 1, 1979, pp. 453-455, vol. 76 No. 3, PNAS, Washington, DC.

Hubacek et al., "Detection of donor DNA after heart transplantation: how far could itbe affected by blood transfusion and donor chimerism?", Transplant Proc., Jun. 2007, pp. 1593-1595, vol. 39, Issue 5, Elsevier, Amsterdam, Netherlands.

Huber, et al., "High-resolution liquid chromatography of DNA fragments on non-porous poly(styrene-divinylbenzene) particles", Nucleic Acids Res., Mar. 11, 1993, pp. 1061-1066, vol. 21 No. 5, Oxford Press, New York, NY.

Intentional search report and written opinion dated Jan. 7, 2013 for PCT/US2012/056416.

International search report and written opinion dated Jan. 26, 2011 for PCT /US20 10/055604.

Kacharmina et al., "Preparation of eDNA from single cells and subcellular regions", Methods Enzymol., 1999, pp. 3-18, vol. 303, Elsevier, Amsterdam, Netherlands.

Karger et al., "DNA Sequencing by Capillary Electrophoresis", Electrophoresis, Jun. 2009, pp. 1-11, 30(Suppl 1), John Wiley & Sons, Inc., Hoboken, NJ.

Kato, et al., "A new packing for separation of DNA restriction fragments by high performance liquid chromatography", J Biochem., Jan. 1, 1984, pp. 83-86, vol. 95, No. 1, Oxford University Press, Oxford, United Kingdom.

Kobashiga et al., "Multicenter intravascular ultrasound validation study amongheart transplant recipients: outcomes after five years", J Am Call Cardiol., May 2005, p. 1532-1537, vol. 45, Issue 9, Journal of the American College of Cardiology, Washington, DC.

Levene et al., "Zero-mode waveguides for single-molecule analysis at high concentrations", Science, Jan. 31, 2003, pp. 682-686, vol. 299, Issue 5607, American Association for the Advancement of Science, Washington, D.C.

Leykin et al., "Comparative linkage analysis and visualization of high-density oligonucleotide SNP array data", BMC Genet., Feb. 15, 2005, pp. 1-16, 6(7), BioMed Central, London, United Kingdom.

Li et al., "Performance Characteristics of 6 Third-Generation Assays for Thyroid-Stimulating Hormone", Clinical Chemistry, Oct. 2005, pp. 1903-1904, vol. 51, No. 10, American Association for Clinical Chemistry, Washington, D.C.

Li et al., "Detection of Donor-Specific DNA Polymorphisms in the Urine of Renal Transplant Recipients", Clinical Chemistry, Apr. 2003, pp. 655-658, vol. 49, Issue 4, American Association for Clinical Chemistry, Washington, DC.

Liu et al., "Algorithms for large-scale genotyping microarrays", Bioinformatics, Dec. 12, 2003, pp. 2397-2403, vol. 19, Issue 18, Oxford University Press, Oxford, United Kingdom.

Livak et al., "Towards fully automated genome-wide polymorphism screening," Nat Genet., Apr. 1995, pp. 341-342, 9(4), Macmillan Publishers Limited, Basingstoke, United Kingdom.

Lo et al., "Plasma nucleic acid analysis by massively parallel sequencing: pathologicalinsights and diagnostic implications", J Pathol., Nov. 2011, pp. 318-323, vol. 225, Issue 3, John Wiley & Sons, Inc., Hoboken, NJ.

Lo et al., "Presence of donor-specific DNA in plasma of kidney and liver-transplant recipients", Lancet, May 2, 1998, pp. 1329-1330, vol. 351, No. 9112, Elsevier, Amsterdam, Netherlands.

Lo et al., "Quantitative analysis of fetal DNA in maternal plasma and serum:implications for noninvasive prenatal diagnosis", Am J Hum Genet., Apr. 1998,pp. 768-775, vol. 62, Issue 4, Elsevier, Amsterdam, Netherlands.

Lo, "Molecular testing of urine: catching DNA on the way out", Clin Chem., Aug. 2000,pp. 1039-1040, vol. 46, Issue 8, American Association for Clinical Chemistry, Washington, DC.

Lo, "Transplantation monitoring by plasma DNA sequencing", Clin Chem., Jul. 2011, pp. 941-942, vol. 57, Issue 7, American Association for Clinical Chemistry, Washington, DC.

Lui et al., "Origin of plasma cell-free DNA after solid organ transplantation", Clin Chem., Mar. 2003, pp. 495-496, vol. 49, Issue 3, American Association for Clinical Chemistry, Washington, DC.

Maheswaran et al., "Detection of mutations in EGFR in circulating lung-cancer cells", N Engl J Med., Jul. 24, 2008, pp. 366-377, 359(4), Massachusetts Medical Society, Waltham, MA.

Mandel et al., "Les acides nucleiques du plasma sanguin chez l'homme", C R Seances Soc Bioi Fil., Feb. 1948, pp. 241-243, 142 (3-4).

Margulies et al., "Genome sequencing in microfabricated high-density picolitre reactors", Nature, Sep. 15, 2005, pp. 376-380, 15;437(7057), Nature Publishing Group, London, United Kingdom.

Moreira et al., "Cell-Free DNA as a Noninvasive Acute Rejection Marker in Renal Transplant", Clin Chem., Nov. 2009, pp. 1958-1966, vol. 55, Issue 11, American Association for Clinical Chemistry, Washington, D.C.

Moudrianakis et al., "Base sequence determination in nucleic acids with the electron microscope, III. Chemistryand microscopy of guanine-labeled DNA", Proc Natl Acad Sci USA, Mar. 1965, pp. 564-571 vol. 53, PNAS, Washington, DC.

Ng et al., "mRNA of placental origin is readily detectable in maternal plasma", Proc Natl Acad Sci USA. Apr. 15, 2003, pp. 4748-4753, vol. 100, No. 8, PNAS, Washington, DC.

Ng et al., "The concentration of circulating corticotropin-releasing hormone mRNA in maternal plasma is increased in preeclampsia",

(56) References Cited

OTHER PUBLICATIONS

Clin Chem., May 2003, pp. 727-731, vol. 49, Issue 5, American Association for Clinical Chemistry, Washington, D.C.
Notice of allowance dated Feb. 12, 2014 for U.S. Appl. No. 13/508,318.
Office action dated May 10, 2013 for U.S. Appl. No. 13/508,318.
Office action dated Nov. 14, 2013 for U.S. Appl. No. 13/508,318.
Pabon et al., "Optimized T7 amplification system for microarray analysis", Biotechniques, Oct. 2001, pp. 874-879, vol. 31, No. 4, New York, NY.
Ruschendorf et al., "ALOHOMORA: a tool for linkage analysis using 10K SNParray data", Bioinformatics, May 1, 2005, pp. 2123-2125, vol. 21, Issue 9, Oxford University Press, Oxford, United Kingdom.
Schwartz et al., "NTera2: a model system to study dopaminergic differentiation ofhuman embryonic stem cells", Stem Cells Dev., Nov. 23, 2005, pp. 517-534, vol. 14, Issue 5, Mary Ann Liebert, Inc., New Rochelle, NY.
Shen et al., "High-throughput SNP genotyping on universal bead arrays", Mutat Res., Jun. 3, 2005, pp. 70-82, vol. 573, Issues 1-2, Elsevier, Amsterdam, Netherlands.
Taylor et al., "Registry of the International Society for Heart and LungTransplantation: twenty-fifth official adult heart transplant report—2008", J Heart Lung Transplant, Sep. 2008, pp. 943-956, vol. 27, Issue 9, Elsevier, Amsterdam, Netherlands.
Tong et al., "Diagnostic developments involving cell-free (circulating) nucleic acids",Clin Chim Acta., Jan. 2006, pp. 187-196, vol. 363, Issues 1-2, Elsevier, Amsterdam, Netherlands.
Van Geldar et al., "Amplified RNA synthesized from limited quantities ofheterogeneous eDNA", Proc Natl Acad Sci USA, Mar. 1, 1990, pp. 1663-1667, vol. 87 No. 5, PNAS, Washington, DC.
Venter, et al., "The sequence of the human genome", Science, Feb. 16, 2001, pp. 1304-1351, vol. 291, American Association for the Advancement of Science, Washington, DC.
Vymetalova et al., "High prevalence of microchimerism in female patients",Transplant Proc., Dec. 2008, pp. 3685-3687, vol. 40, Issue 10, Elsevier, Amsterdam, Netherlands.
Warren et al., "Transcription factor profiling in individual hematopoietic progenitorsby digital RT-PCR", Proc Natl Acad Sci USA, Nov. 21, 2006, pp. 17807-17812, vol. 103 No. 47, PNAS, Washington, DC.
Zhang et al., "Presence of donor- and recipient-derived DNA in cell-free urine samples of renal transplantation recipients: urinary DNA chimerism", Clin Chem., Oct. 1999, pp. 1741-1746, vol. 45, Issue 10, American Association for Clinical Chemistry, Washington, DC.
Zheng et al., "Nonhematopoietically derived DNA is shorter than hematopoieticallyderived DNA in plasma: a transplantation model", Clin Chem., Mar. 2012, pp. 549-558, vol. 58, Issue 3, American Association for Clinical Chemistry, Washington, DC.
Zhong et al., "Cell-free DNA in urine: a marker for kidney graft rejection, but not forprenatal diagnosis?", Ann NY Acad Sci., Sep. 2001, pp. 250-257, vol. 945, John Wiley & Sons, Inc., Hoboken, NJ.
Illumina, "Genomic Sequencing", Data Sheet: Sequencing, 2010, pp. 1-6, Illumina, San Diego, CA.
Ansorge., "Next-generation DNA sequencing techniques", New Biotechnology, Apr. 2009, pp. 195-203, vol. 25, Issue 4, Elsevier, Amsterdam, Netherlands.
Karger et al., "DNA Sequencing by Capillary Electrophoresis", Electrophoresis, Jun. 2009, pp. 196-202, 30, Supp 1, Wiley, Hoboken, NJ.
Girnita et al., "Disparate distribution of 16 candidate single nucleotide polymorphisms among racial and ethnic groups of pediatric heart transplant patients", Transplanation, Dec. 27, 2006, pp. 1774-1780, vol. 82, Issue 12, Lippincott Williams & Wilkins, Philadelphia, PA.
Ayala et al., "Long-term follow-up of donor chimerism and tolerance after human liver transplantation", AASLD Liver Transplantation, May 28, 2009, pp. 581-591, vol. 15, Issue 6, American Association for the Study of Liver Diseases, Alexandria, Virginia.
Lui et al., "Origin of plasma cell-free DNA after solid organ transplantation", Clinical Chemistry, Mar. 2003, pp. 495-496, vol. 49, Issue 3, American Association for Clinical Chemistry, Washington, D.C.
Science Direct., "Single-nucleotide Polymorphism", Emery and Rimoins Principle's and Practice of Medical Genetics, 2013, https://www.sciencedirect.com/topics/neuroscience/single-nucleotide-polymorphism Downloaded Sep. 26, 2018, pp. 1-7, Elsevier, Amsterdam, Netherlands.
Horowitz et al., "Detection of Cardiac Allograft Rejection and Response to Immunosuppressive Therapy With Peripheral Blood Gene Expression", Molecular Cardiology, Dec. 21-28, 2004, pp. 3815-3821, American Heart Association, Dallas, TX.
Ying et al., "Detection of Donor-specific DNA Polymorphisms in the Urine of Renal Transplant Recipients", Clinical Chem., Apr. 2003, pp. 655-658, vol. 49, Issue 4, American Association for Clinical Chemistry, Washington, D.C.
European search report with written opinion dated Oct. 28, 2018, 6 Pages, for EP10829142.
Li et al., "Ready detection of donor-specific single-nucleotide polymorphisms in the urine of renal transplant recipients by matrix-assisted laser desorption/ionization time-of-flight mass spectrometry", Clin Chem., Oct. 2005, pp. 1903-1904, vol. 51, Issue 10, American Association for Clinical Chemistry, Washington, D.C.
Notice of allowance dated Oct. 2, 2017, 16 Pages for U.S. Appl. No. 14/188,455.
Final Office action dated Feb. 28, 2017, 25 Pages for U.S. Appl. No. 14/188,455.
Office action dated Aug. 11, 2016, 38 Pages for U.S. Appl. No. 14/188,455.
Office Action dated Oct. 2, 2018, 46 Pages for U.S. Appl. No. 16/110,646.
Lo et al., "Digital PCR for the molecular detection of fetal chromosomal aneuploidy." PNAS. 104(32):13116-13121 (2007).
Gadi et al. (2006) "Soluble Donor DNA Concentrations in Recipient Serum Correlate with Pancreas-Kidney Rejection" vol. 52, No. 3, pp. 379-382.
Li et al (1999) "Presence of Donor- and Recipient-derived DNA in Cell-free Urine Samples of Renal Transplantation Recipients: Urinary DNA Chimerism", vol. 45, No. 10, pp. 1741-1746.
Mashayekhi et al., Analysis of Read Length Limiting Factors in Pyrosequencing Chemistry, Analytical Biochemistry, 2007, 363, 275-287.
Lo et al (2000) "Fetal DNA in Maternal Plasma: Biology and Diagnostic Applications" Clinical Chemistry, 46(12): 1903-1906.
Lo et al. (1998) "Quantitative analysis of fetal DNA in maternal plasma and serum: implications for noninvasive prenatal diagnosis", Am. J. Hum. Genet., 62: 768-775.
Hochberg et al. (2003) "A Novel Rapid Single Nucleotide Polymorphism (SN P)-Based Method for Assessment of Hematopoietic Chimerism After Allogenic Stem Cell Transplantation" Blood, 101(1): 363-369.
Willasch et al. (2007) "Sequence Polymorphism Systems for Quantitative Real-Time Polymerase Chain Reaction to Characterize Hematopoietic Chimerism—High Informativity and Sensitivity as Well as Excellent Reproducibility and Precision of Measurement" Laboratory Hematology, 13: 73-84.
Harismedny et al. (2009) "Evaluation of Next Generation Sequencing Platforms for Population Targeted Sequencing Studies" Genome Biology, 10(R32), 1-13.
Yanni et al. (2003) "Origin of Plasma Cell-Free DNA After Solid Organ Transplantation" Clinical Chern, 43(3): 495-496.
Merrian-Webster, Tolerance, Merriam-Webster Dictionary, 2020, lines 1-2; obtained from https://www.merriam-webster.com/dictionary/endurance#synonyms on Sep. 23, 2020. (Year: 2020).
Lo et al (2007) "Prenatal diagnosis: progress through plasma nucleic acids" Nature Reviews Genetics vol. 8, pp. 71-77.

* cited by examiner

| Library | 0% Donor | 1% Donor | 3% Donor | 10% Donor |
|---|---|---|---|---|
| Total Unique Aligned Reads | 8747074 | 9340382 | 5444089 | 8485355 |
| Total w/ SNPs | 80301 | 84525 | 40161 | 71286 |
| # Homo for Recip. | 19882 | 20571 | 9269 | 15367 |
| # Homo for Donor | 77 | 133 | 360 | 1936 |

SEQUENCE LISTING

<160> NUMBER OF SEQ ID NOS: 3

<210> SEQ ID NO 1
<211> LENGTH: 216
<212> TYPE: DNA
<213> ORGANISM: H. sapiens

<400> SEQUENCE: 1

```
aacgcgtaat cgagtcgtac gtaaagcggg tgttcgaaga ggttgaccgg ggagagtctg      60
atcggctgca ggttggttgt gctgactgtt tcgtgaaacg tacgctgtcc gcgtagtagc     120
tggttgatca cgacactacg atccacgact ttacgactgg actgactgac tacgatcgac     180
cgactttacg actggactga ctgactagga tcgact                               216
```

<210> SEQ ID NO 2
<211> LENGTH: 109
<212> TYPE: DNA
<213> ORGANISM: H. sapiens

<400> SEQUENCE: 2

```
ggttgaccgg gagagtctga tccgcgtagt agctggttga tcaaacgcgc gagcgctagc      60
gaagcatttc tctcccgcta cggccgatga ctgactgact aggatcgac                 109
```

<210> SEQ ID NO 3
<211> LENGTH: 21
<212> TYPE: DNA
<213> ORGANISM: H. sapiens

<400> SEQUENCE: 3

```
tgactgactg acacgatcga c                                                21
```

NUCLEIC ACID SEQUENCING APPARATUS FOR MONITORING STATUS OF A TRANSPLANT RECIPIENT

CROSS REFERENCE

This application claims benefit and is a Continuation of application Ser. No. 15/788,549 filed Oct. 19, 2017, which is a Continuation of application Ser. No. 14/188,455 filed Feb. 24, 2014, now U.S. Pat. No. 9,845,497, issued Dec. 19, 2019, which is a Continuation of application Ser. No. 13/508,318 filed Jul. 19, 2012, now patented as U.S. Pat. No. 8,703,652 issued Apr. 22, 2014, which is a 371 application and claims the benefit of PCT Application No. PCT/US2010/055604, filed Nov. 5, 2010, which claims benefit of U.S. Provisional Patent Application No. 61/280,674, filed Nov. 6, 2009, which applications are incorporated herein by reference in their entirety.

FEDERALLY SPONSORED RESEARCH AND DEVELOPMENT

This invention was made with Government support under contracts HL099995 and OD000251 awarded by the National Institutes of Health. The Government has certain rights in the invention.

BACKGROUND OF THE INVENTION

Organ transplantation is an important medical procedure which saves lives in cases where a patient has organ failure or disablement, and it is now possible to transplant many organs including heart, lungs, kidney, and liver. In some cases, the transplanted organ is rejected by the recipient patient, which creates a life-threatening situation. Monitoring the patient for rejection is difficult and expensive, often requiring invasive procedures. Furthermore, current surveillance methods lack adequate sensitivity.

The present invention resolves these problems by providing non-invasive methods of monitoring organ transplant patients for rejection that are sensitive, rapid and inexpensive.

SUMMARY OF THE INVENTION

The invention provides methods, devices, compositions and kits for diagnosing and/or predicting transplant status or outcome in a subject who has received a transplant. In some embodiments, the invention provides methods of diagnosing or predicting transplant status or outcome comprising the steps of: (i) providing a sample from a subject who has received a transplant from a donor; (ii) determining the presence or absence of one or more nucleic acids from the donor transplant, where the one or more nucleic acids from the donor are identified based on a predetermined marker profile; and (iii) diagnosing or predicting transplant status or outcome based on the presence or absence of the one or more nucleic acids.

In some embodiments, the transplant status or outcome comprises rejection, tolerance, non-rejection based allograft injury, transplant function, transplant survival, chronic transplant s injury, or titer pharmacological immunosuppression. In some embodiments, the non-rejection based allograft injury is selected from the group of ischemic injury, virus infection, peri-operative ischemia, reperfusion injury, hypertension, physiological stress, injuries due to reactive oxygen species and injuries caused by pharmaceutical agents.

In some embodiments, the sample is selected from the group consisting of blood, serum, urine, and stool. In some embodiments, the marker profile is a polymorphic marker profile. In some embodiments, the polymorphic marker profile comprises one or more single nucleotide polymorphisms (SNP's), one or more restriction fragment length polymorphisms (RFLP's), one or more short tandem repeats (STRs), one or more variable number of tandem repeats (VNTR's), one or more hypervariable regions, one or more minisatellites, one or more dinucleotide repeats, one or more trinucleotide repeats, one or more tetranucleotide repeats, one or more simple sequence repeats, or one or more insertion elements. In some embodiments, the polymorphic marker profile comprises one or more SNPs In some embodiments, the marker profile is determined by genotyping the transplant donor. In some embodiments, the methods further comprise genotyping the subject receiving the transplant. In some embodiments, the methods further comprise establishing a profile of markers, where the markers are distinguishable between the transplant donor and the subject receiving the transplant. In some embodiments, the genotyping is performed by a method selected from the group consisting of sequencing, nucleic acid array and PCR.

In any of the embodiments described herein, the transplant graft maybe any solid organ and skin transplant. In some embodiments, the transplant is selected from the group consisting of kidney transplant, heart transplant, liver transplant, pancreas transplant, lung transplant, intestine transplant and skin transplant.

In some embodiments, the nucleic acid is selected from the group consisting of double-stranded DNA, single-stranded DNA, single-stranded DNA hairpins, DNA/RNA hybrids, RNA and RNA hairpins. In some embodiments, the nucleic acid is selected from the group consisting of double-stranded DNA, single-stranded DNA and cDNA. In some embodiments, the nucleic acid is mRNA. In some embodiments, the nucleic acid is obtained from circulating donor cells. In some embodiments, the nucleic acid is circulating cell-free DNA.

In some embodiments, the presence or absence of the one or more nucleic acids is determined by a method selected from the group consisting of sequencing, nucleic acid array and PCR. In some embodiments, the sequencing is shotgun sequencing. In some embodiments, the array is a DNA array. In some embodiments, the DNA array is a polymorphism array. In some embodiments, the polymorphism array is a SNP array.

In some embodiments, the methods further comprise quantitating the one or more nucleic acids. In some embodiments, the amount of the one or more nucleic acids is indicative of transplant status or outcome. In some embodiments, the amount of the one or more nucleic acids above a predetermined threshold value is indicative of a transplant status or outcome. In some embodiments, the threshold is a normative value for clinically stable post-transplantation patients with no evidence of transplant rejection or other pathologies. In some embodiments, there are different predetermined threshold values for different transplant outcomes or status. In some embodiments, temporal differences in the amount of the one or more nucleic acids are indicative of a transplant status or outcome.

In some embodiments, the methods described herein have at least 56% sensitivity. In some embodiments, the methods described herein have at least 78% sensitivity. In some embodiments, the methods described herein have a specificity of about 70% to about 100%. In some embodiments, the methods described herein have a specificity of about 80% to about 100%. In some embodiments, the methods described herein a specificity of about 90% to about 100%. In some embodiments, the methods described herein have a specificity of about 100%.

In some embodiments, the invention provides computer readable mediums comprising: a set of instructions recorded thereon to cause a computer to perform the steps of: (i) receiving data from one or more nucleic acids detected in a sample from a subject who has received transplant from a donor, where the one or more nucleic acids are nucleic acids from the donor transplant, and where the one or more nucleic acids from the donor are identified based on a predetermined marker profile; and (ii) diagnosing or predicting transplant status or outcome based on the presence or absence of the one or more nucleic acids.

In some embodiments, the invention provides reagents and kits thereof for practicing one or more of the methods described herein.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
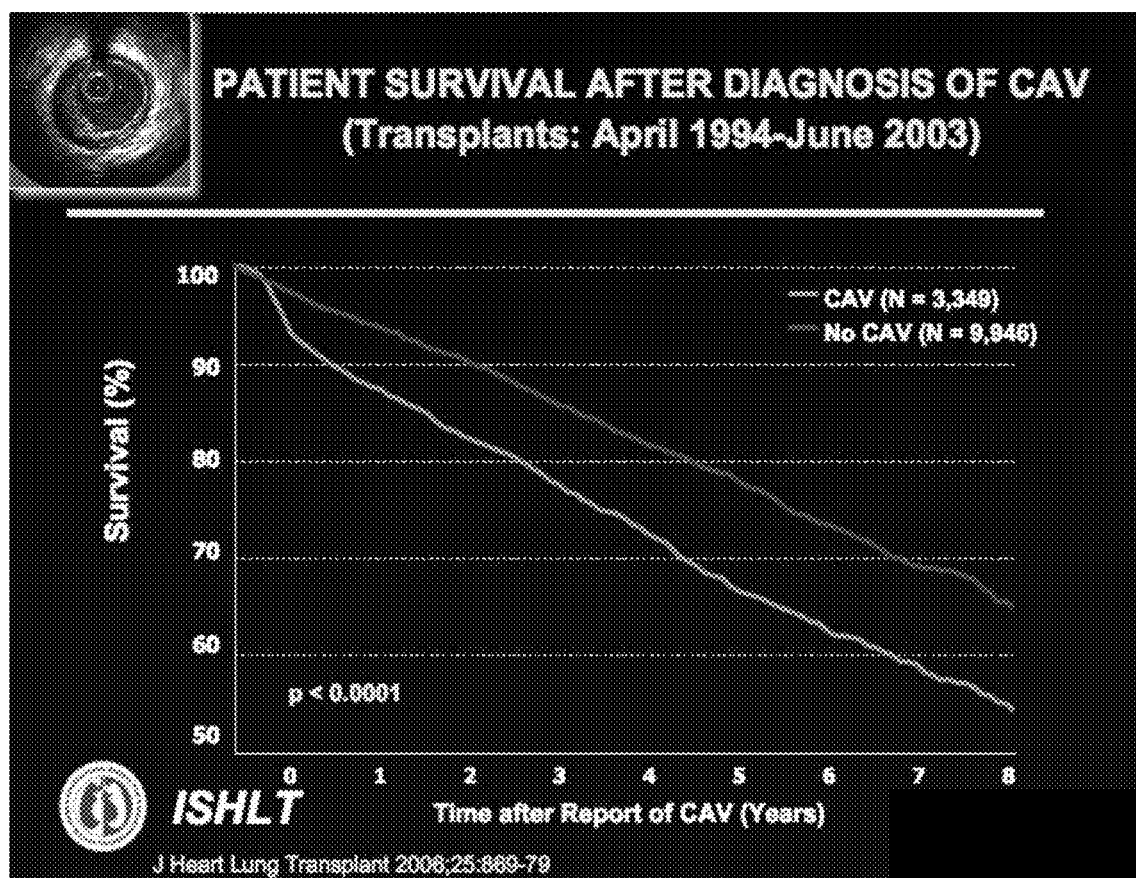
FIG. 1 shows patient survival after diagnosis of CAV.

Reference will now be made in detail to particularly preferred embodiments of the invention. Examples of the preferred embodiments are illustrated in the following Examples section.

Unless defined otherwise, all technical and scientific terms used herein have the same meaning as is commonly understood by one of skill in the art to which this invention belongs. All patents and publications referred to herein are incorporated by reference in their entirety.

Methods, devices, compositions and kits are provided for diagnosing or predicting transplant status or outcome in a subject who has received a transplant. The transplant status or outcome may comprise rejection, tolerance, non-rejection based transplant injury, transplant function, transplant survival, chronic transplant injury, or titer pharmacological immunosuppression.

This invention describes sensitive and non-invasive methods, devices, compositions and kits for monitoring organ transplant patients, and/or for diagnosing or predicting transplant status or outcome (e.g. transplant rejection). In some embodiments, the methods, devices, compositions and kits are used to establish a genotype for both the donor and the recipient before transplantation to enable the detection of donor-specific nucleic acids such as DNA or RNA in bodily fluids such as blood or urine from the organ recipient after transplantation.

In some embodiments, the invention provides methods of determining whether a patient or subject is displaying transplant tolerance. The term "transplant tolerance" includes when the subject does not reject a graft organ, tissue or cell(s) that has been introduced into/onto the subject. In other words, the subject tolerates or maintains the organ, tissue or cell(s) that has been transplanted to it. The term "patient" or "subject" as used herein includes humans as well as other mammals.

In some embodiments the invention provides methods for diagnosis or prediction of transplant rejection. The term "transplant rejection" encompasses both acute and chronic transplant rejection. "Acute rejection or AR" is the rejection by the immune system of a tissue transplant recipient when the transplanted tissue is immunologically foreign. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery. Generally, acute rejection can be inhibited or suppressed with immunosuppressive drugs such as rapamycin, cyclosporin A, anti-CD40L monoclonal antibody and the like.

"Chronic transplant rejection or CR" generally occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs.

In some embodiments, the invention further includes methods for determining an immunosuppressive regimen for a subject who has received a transplant, e.g., an allograft.

Certain embodiments of the invention provide methods of predicting transplant survival in a subject that has received a transplant. The invention provides methods of diagnosing or predicting whether a transplant in a transplant patient or subject will survive or be lost. In certain embodiments, the invention provides methods of diagnosing or predicting the presence of long-term graft survival. By "long-term" graft survival is meant graft survival for at least about 5 years beyond current sampling, despite the occurrence of one or more prior episodes of acute rejection. In certain embodiments, transplant survival is determined for patients in which at least one episode of acute rejection has occurred. As such, these embodiments provide methods of determining or predicting transplant survival following acute rejection. Transplant survival is determined or predicted in certain embodiments in the context of transplant therapy, e g, immunosuppressive therapy, where immunosuppressive therapies are known in the art. In yet other embodiments, methods of determining the class and/or severity of acute rejection (and not just the presence thereof) are provided.

In some embodiments, the invention provides methods for diagnosis or prediction of non-rejection based transplant injury. Examples of non-rejection based graft injury include, but are not limited to, ischemic injury, virus infection, pen-operative ischemia, reperfusion injury, hypertension, physiological stress, injuries due to reactive oxygen species and injuries caused by pharmaceutical agents.

As in known in the transplantation field, the transplant organ, tissue or cell(s) may be allogeneic or xenogeneic, such that the grafts may be allografts or xenografts. A feature of the graft tolerant phenotype detected or identified by the subject methods is that it is a phenotype which occurs without immunosuppressive therapy, i.e., it is present in a host that is not undergoing immunosuppressive therapy such that immunosuppressive agents are not being administered to the host. The transplant graft maybe any solid organ and skin transplant. Examples of organ transplants that can be analyzed by the methods described herein include but are not limited to kidney transplant, pancreas transplant, liver transplant, heart transplant, lung transplant, intestine transplant, pancreas after kidney transplant, and simultaneous pancreas-kidney transplant.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M.J. MacPherson, B.D. Hames and G.R. Taylor eds. (1995)), Harlow and Lane, eds. (1988) ANTIBODIES, A LABORATORY MANUAL, and ANIMAL CELL CULTURE (R.I. Freshney, ed. (1987)).

INTRODUCTION

Methods, devices, compositions and kits are provided for diagnosing or predicting transplant status or outcome in a subject who has received a transplant.

As mention above, monitoring transplant patients for transplant status or outcome is difficult and expensive, often requiring non-sensitive and invasive procedures. For instance, in heart transplant patients acute rejection surveillance requires serial endomyocardial biopsies that are routinely performed at weekly and monthly intervals during the initial year after transplant, with a total of 6-8 biopsies in most patients. Advances in immunosuppression, rejection surveillance, and early recognition and treatment of life-threatening infections have led to continuous improvements in early outcomes after cardiac transplantation. (Taylor, D. O., et al., *J Heart Lung Transplant*, 27, 943-956 (2008)) However, there has not been a similar improvement in late mortality, which is largely attributable to cardiac allograft vasculopathy (CAV). (FIG. 1) Today, CAV remains the major cause of late graft failure and death amongst the nearly 22,000 living heart transplant recipients in the United States. Early detection of CAV, prior to the development of angiographically apparent disease, graft dysfunction, or symptom onset is important because patient mortality after detection by coronary angiography (the standard of care) is unacceptably high, with 2-year mortality rates of 50% having been reported. Current surveillance methods for CAV lack adequate sensitivity or require invasive procedures and the most commonly applied method, coronary angiography, lacks sensitivity (Kobashigawa, J. A., et al., J Am Coll Cardiol, 45, 1532-1537 (2005)). Delayed diagnosis due to underestimation of disease severity is a feature of coronary angiography that is largely overcome by intravascular ultrasound (IVUS). (Fitzgerald, P. J., et al., *Circulation,* 86, 154-158 (1992)) However, both of these invasive left-heart, arterial catheter methods are costly, resource intensive, and associated with significant risk of morbidity and patient discomfort. Early detection of CAV, prior to the development of angiographically apparent disease, graft dysfunction, or symptom onset is crucial to guide the appropriate use of emerging therapies that retard and occasionally reverse progression of CAV. The development of markers for early, non-invasive, safe, and cost-effective detection of acute rejection and CAV, and their rapid translation to a practical and reliable test that can be used in the clinic represents a major unmet medical need for the nearly 22,000 living heart transplant recipients in the United States, and a similar number worldwide.

The pressing need for early diagnosis and risk stratification is further underscored by recent studies demonstrating delayed progression and/or reversal of CAV following intervention with newer immunosuppressive regimens. Since the use of these newer therapies are encumbered by adverse effects, drug interactions, and cost, it is important to identity the patients in whom the benefits outweigh the risks. Aside from its impact on mortality and morbidity, CAV surveillance is costly in terms of resource utilization and potential for patient complications. Given the current standard of care to perform annual coronary angiography for the initial five years after heart transplantation, each patient surviving to year 5 will have received 4 angiograms for an average fully loaded cost of $25,000 per angiogram. Since the 5-year survival rate after heart transplantation is 72%, approximately 1,440 patients out of the 2,000 patients receiving heart transplants each year will undergo 4 procedures for a total of at least 5,760 procedures. At an average cost of $25,000 per coronary angiogram, this will amount to $144,000,000 per year in healthcare dollars for monitoring patients after heart transplantation. A non-invasive test that identifies the patients at low risk of CAV would mean that coronary angiography could be safely avoided in this group, thereby considerably reducing the cost of their long-term management.

The same difficulties and expenses are experienced by patients receiving other type of transplants.

a. Circulating Nucleic Acids

Circulating, or cell-free, DNA was first detected in human blood plasma in 1948. (Mandel, P. Metais, P., C R Acad. Sci. Paris, 142, 241-243 (1948)) Since then, its connection to disease has been established in several areas. (Tong, Y. K. Lo, Y. M., Clin Chim Acta, 363, 187-196 (2006)) Studies reveal that much of the circulating nucleic acids in blood arise from necrotic or apoptotic cells (Giacona, M. B., et al., Pancreas, 17, 89-97 (1998)) and greatly elevated levels of nucleic acids from apoptosis is observed in diseases such as cancer. (Giacona, M. B., et al., Pancreas, 17, 89-97 (1998); Fournie, G. J., et al., Cancer Lett, 91, 221-227 (1995)) Particularly for cancer, where the circulating DNA bears hallmark signs of the disease including mutations in oncogenes, microsatellite alterations, and, for certain cancers, viral genomic sequences, DNA or RNA in plasma has become increasingly studied as a potential biomarker for disease. For example, Diehl et al recently demonstrated that a quantitative assay for low levels of circulating tumor DNA in total circulating DNA could serve as a better marker for detecting the relapse of colorectal cancer compared with carcinoembryonic antigen, the standard biomarker used clinically. (Diehl, F., et al., Proc Natl Acad Sci, 102, 16368-16373 (2005); Diehl, F., et al., Nat Med, 14, 985-990 (2008)) Maheswaran et al reported the use of genotyping of circulating cells in plasma to detect activating mutations in epidermal growth factor receptors in lung cancer patients that would affect drug treatment. (Maheswaran, S., et al., N Engl J Med, 359, 366-377 (2008)) These results collectively establish both circulating DNA, either free in plasma or from circulating cells, as a useful species in cancer detection and treatment. Circulating DNA has also been useful in healthy patients for fetal diagnostics, with fetal DNA circulating in maternal blood serving as a marker for gender, rhesus D status, fetal aneuploidy, and sex-linked disorders. Fan et al recently demonstrated a strategy for detecting fetal aneuploidy by shotgun sequencing of cell-free DNA taken from a maternal blood sample, a methodology that can replace more invasive and risky techniques such as amniocentesis or chorionic villus sampling. (Fan, H. C., Blumenfeld, Y. J., Chitkara, U., Hudgins, L., Quake, S. R., Proc Natl Acad Sci, 105, 16266-16271 (2008))

In all these applications of circulating nucleic acids, the presence of sequences differing from a patient's normal genotype has been used to detect disease. In cancer, mutations of genes are a tell-tale sign of the advance of the disease; in fetal diagnostics, the detection of sequences specific to the fetus compared to maternal DNA allows for analysis of the health of the fetus.

In some embodiments, the invention provides non-invasive diagnostics exists for organ transplant patients where sequences from the organ donor, otherwise "foreign" to the patient, can be quantitated specifically. Without intending to be limited to any theory, as cell-free DNA or RNA often arises from apoptotic cells, the relative amount of donor-specific sequences in circulating nucleic acids should provide a predictive measure of on-coming organ failure in transplant patients for many types of solid organ transplantation including, but not limited to, heart, lung, liver, and kidney.

b. Circulating Nucleic Acids and Transplant Rejection

In some embodiments, the invention provides methods, devices, compositions and kits for detection and/or quantitating circulating nucleic acids, either free in plasma or from circulating cells, for the diagnosis, prognosis, detection and/or treatment of a transplant status or outcome. There have been claims of detection of donor-DNA in sex-mismatched liver and kidney transplant patients; conventional PCR was used to search for Y chromosome sequences from male donors in the blood of female patients. (Lo, Y. M., et al., Lancet, 351, 1329-1330 (1998) However, in a follow-on study Y-chromosome specific sequences were not detected above background in 16 out of 18 patients using a more accurate quantitative polymerase chain reaction (qPCR) assay. (Lui, Y. Y., et al., Clin Chem, 49, 495-496 (2003)) In renal transplantation, urine samples of similarly sex-mismatched transplant patients were analyzed and Y chromosomal DNA was detected in patients immediately after transplantation as well as during graft rejection episodes. (Zhang, J., et al., Clin Chem, 45, 1741-1746 (1999); Zhong, X. Y., et al., Ann N Y Acad Sci, 945, 250-257 (2001))

Figure 2:
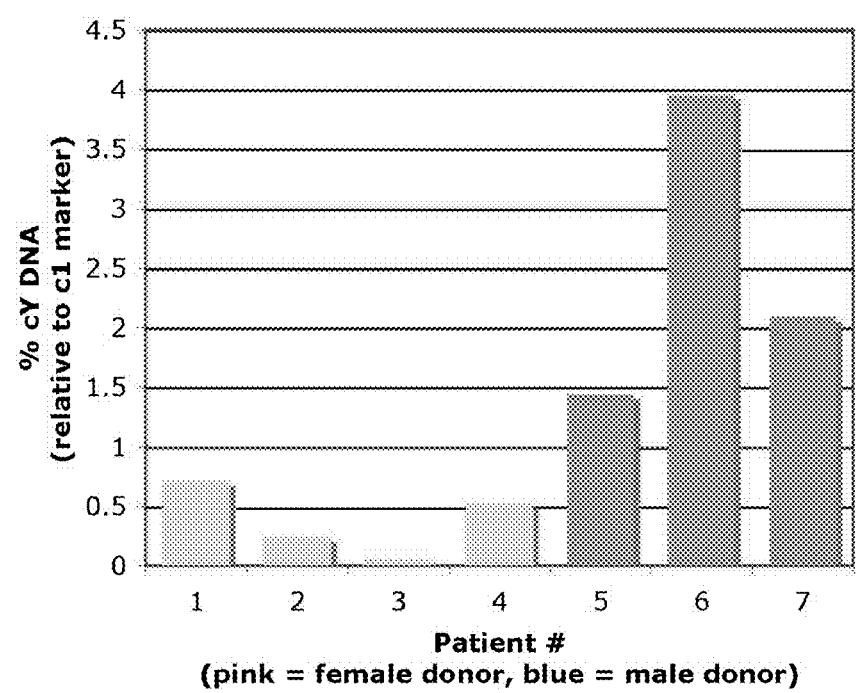
FIG. 2 shows detection of donor DNA in patients receiving gender mismatched transplants.

Example 1 examined gender-mismatched heart transplant recipients and applied digital PCR (Warren, L., Bryder, D., Weissman, I. L., Quake, S. R., Proc Natl Acad Sci, 103, 17807-17812 (2006); Fan, H. C. Quake, S. R., Anal Chem, 79, 7576-7579 (2007)) to detect the level of donor-derived chromosome Y signal in plasma samples taken at the same time that an endomyocardial biopsy determined a grade 3A or 3B rejection episode. While there was not any significant chromosome Y signal detected from four control female-to-female transplant patients, 1.5-8% total genomic fraction for chromosome Y signals at the rejection time points was observed for three male-to-female transplant patients across four rejection episodes (FIG. 2). A time-course study for one of these patients revealed that the level of chromosome Y detected in plasma was neglible in plasma at three months prior to rejection, but increased >10-fold to 2% of total genomic fraction at the time a biopsy determined rejection (See FIGS. 3 and 4). Collectively, these results establish that for heart transplant patients, donor-derived DNA present in plasma can serve as a potential marker for the onset of organ failure.

While each of these studies demonstrates donor-DNA in bodily fluids for different solid organ transplants, they are all limited to the special case of females receiving organs from males and will not work for females receiving from females, males receiving from males, or males receiving from females. Further problems with this strategy arise from the prevalence of microchimerism in female patients where past male pregnancies or blood transfusions may lead to Y-chromosome specific signals from sources other than the transplanted organ. (Hubacek, J. A., Vymetalova, Y., Bohuslavova, R., Kocik, M., Malek, I., Transplant Proc, 39, 1593-1595 (2007); Vymetalova, Y., et al., Transplant Proc, 40, 3685-3687 (2008)) The detection of donor-specific human leukocyte antigen (HLA) alleles in circulating DNA has been considered as a signal for organ rejection, specifically for kidney and pancreas transplant patients. (Gadi, V. K., Nelson, J. L., Boespflug, N. D., Guthrie, K. A., Kuhr, C. S., Clin Chem, 52, 379-382 (2006)) However, this strategy will also be limited by the inability to distinguish HLA alleles between all donors and recipients, particularly for common HLA types, and the potential complication of microchimerism such as from blood transfusions. (Baxter-Lowe, L. A. Busch, M. P., Clin Chem, 52, 559-561 (2006))

In some embodiments, the invention provides a universal approach to noninvasive detection of graft rejection in transplant patients which circumvents the potential problems of microchimerism from DNA from other foreign sources and is general for all organ recipients without consideration of gender. In some embodiments, a genetic fingerprint is generated for the donor organ. This approach allows for a reliable identification of sequences arising solely from the organ transplantation that can be made in a manner that is independent of the genders of donor and recipient.

In some embodiments, both the donor and recipient will be genotyped prior to transplantation. Examples of methods that can be used to genotyped the transplant donor and the transplant recipient include, but are not limited to, whole genome sequencing, exome sequencing, or polymorphisms arrays (e.g., SNP arrays). A set of relevant and distinguishable markers between the two sources is established. In some embodiments, the set of markers comprises a set of polymorphic markers. Polymorphic markers include single nucleotide polymorphisms (SNP's), restriction fragment length polymorphisms (RFLP's), short tandem repeats (STRs), variable number of tandem repeats (VNTR's), hypervariable regions, minisatellites, dinucleotide repeats, trinucleotide repeats, tetranucleotide repeats, simple sequence repeats, and insertion elements such as Alu. In some embodiments, the set of markers comprises SNPs.

Following transplantation, bodily fluid such as blood can be drawn from the patient and analyzed for markers. Examples of bodily fluids include, but are not limited to, smears, sputum, biopsies, secretions, cerebrospinal fluid, bile, blood, lymph fluid, saliva, and urine. Detection, identification and/or quantitation of the donor-specific markers (e.g. polymorphic markers such as SNPs) can be performed using real-time PCR, chips (e.g., SNP chips), high-throughput shotgun sequencing of circulating nucleic acids (e.g. cell-free DNA), as well as other methods known in the art including the methods described herein. The proportion of donor nucleic acids can be monitored over time and an increase in this proportion can be used to determine transplant status or outcome (e.g. transplant rejection).

In some embodiments, where the transplant is a xenotransplant, detection, identification and/or quantitation of the donor-specific markers can be performed by mapping one or more nucleic acids (e.g., DNA) to the genome of the specie use to determine whether the one or more nucleic acids come from the transplant donor. Polymorphic markers as described above can also be used where the transplant is a xenotransplant.

In any of the embodiments described herein, the transplant graft can be any solid organ or skin transplant. Examples of organ transplants that can be analyzed by the methods described herein include but are not limited to kidney transplant, pancreas transplant, liver transplant, heart transplant, lung transplant, intestine transplant, pancreas after kidney transplant, and simultaneous pancreas-kidney transplant.

Samples

In some embodiments, the methods described herein involve performing one or more genetic analyses or detection steps on nucleic acids. In some embodiments target nucleic acids are from a sample obtained from a subject that has received a transplant. Such subject can be a human or a domesticated animal such as a cow, chicken, pig, horse, rabbit, dog, cat, or goat. In some embodiments, the cells used in the present invention are taken from a patient. Samples derived from an animal, e.g., human, can include, for example whole blood, sweat, tears, saliva, ear flow, sputum, lymph, bone marrow suspension, lymph, urine, saliva, semen, vaginal flow, cerebrospinal fluid, brain fluid, ascites, milk, secretions of the respiratory, intestinal or genitourinary tracts fluid, a lavage of a tissue or organ (e.g. lung) or tissue which has been removed from organs, such as breast, lung, intestine, skin, cervix, prostate, pancreas, heart, liver and stomach. For example, a tissue sample can comprise a region of functionally related cells or adjacent cells. Such samples can comprise complex populations of cells, which can be assayed as a population, or separated into sub-populations. Such cellular and acellular samples can be separated by centrifugation, elutriation, density gradient separation, apheresis, affinity selection, panning, FACS, centrifugation with Hypaque, etc. By using antibodies specific for markers identified with particular cell types, a relatively homogeneous population of cells may be obtained. Alternatively, a heterogeneous cell population can be used. Cells can also be separated by using filters. For example, whole blood can also be applied to filters that are engineered to contain pore sizes that select for the desired cell type or class. Cells can be filtered out of diluted, whole blood following the lysis of red blood cells by using filters with pore sizes between 5 to 10 μm, as disclosed in U.S. patent application Ser. No. 09/790,673. Other devices can separate cells from the bloodstream, see Demirci U, Toner M., Direct etch method for microfluidic channel and nano-height post-fabrication by picoliter droplets, Applied Physics Letters 2006; 88 (5), 053117; and Irimia D, Geba D, Toner M., Universal microfluidic gradient generator, Analytical Chemistry 2006; 78: 3472-3477. Once a sample is obtained, it can be used directly, frozen, or maintained in appropriate culture medium for short periods of time. Methods to isolate one or more cells for use according to the methods of this invention are performed according to standard techniques and protocols well-established in the art.

To obtain a blood sample, any technique known in the art may be used, e.g. a syringe or other vacuum suction device. A blood sample can be optionally pre-treated or processed prior to enrichment. Examples of pre-treatment steps include the addition of a reagent such as a stabilizer, a preservative, a fixant, a lysing reagent, a diluent, an anti-apoptotic reagent, an anti-coagulation reagent, an anti-thrombotic reagent, magnetic property regulating reagent, a buffering reagent, an osmolality regulating reagent, a pH regulating reagent, and/or a cross-linking reagent.

When a blood sample is obtained, a preservative such an anti-coagulation agent and/or a stabilizer can be added to the sample prior to enrichment. This allows for extended time for analysis/detection. Thus, a sample, such as a blood sample, can be analyzed under any of the methods and systems herein within 1 week, 6 days, 5 days, 4 days, 3 days, 2 days, 1 day, 12 hrs, 6 hrs, 3 hrs, 2 hrs, or 1 hr from the time the sample is obtained.

In some embodiments, a blood sample can be combined with an agent that selectively lyses one or more cells or components in a blood sample. For example platelets and/or enucleated red blood cells are selectively lysed to generate a sample enriched in nucleated cells. The cells of interest can subsequently be separated from the sample using methods known in the art.

When obtaining a sample from a subject (e.g., blood sample), the amount can vary depending upon subject size and the condition being screened. In some embodiments, up to 50, 40, 30, 20, 10, 9, 8, 7, 6, 5, 4, 3, 2, or 1 mL of a sample is obtained. In some embodiments, 1-50, 2-40, 3-30, or 4-20 mL of sample is obtained. In some embodiments, more than 5, 10, 15, 20, 25, 30, 35, 40, 45, 50, 55, 60, 65, 70, 75, 80, 85, 90, 95 or 100 mL of a sample is obtained.

Nucleic Acids

Nucleic acids from samples that can be analyzed by the methods herein include: double-stranded DNA, single-stranded DNA, single-stranded DNA hairpins, DNA/RNA hybrids, RNA (e.g. mRNA or miRNA) and RNA hairpins. Examples of genetic analyses that can be performed on nucleic acids include e.g., sequencing, SNP detection, STR detection, RNA expression analysis, and gene expression.

In some embodiments, less than 1 pg, 5 pg, 10 pg, 20 pg, 30 pg, 40 pg, 50 pg, 100 pg, 200 pg, 500 pg, 1 ng, 5 ng, 10 ng, 20 ng, 30 ng, 40 ng, 50 ng, 100 ng, 200 ng, 500 ng, 1 ug, 5 ug, 10 ug, 20 ug, 30 ug, 40 ug, 50 ug, 100 ug, 200 ug, 500 ug or 1 mg of nucleic acids are obtained from the sample for further genetic analysis. In some cases, about 1-5 pg, 5-10 pg, 10-100 pg, 100 pg-1 ng, 1-5 ng, 5-10 ng, 10-100 ng, 100 ng-1 ug of nucleic acids are obtained from the sample for further genetic analysis.

In some embodiments, the methods described herein are used to detect and/or quantified a target nucleic acid molecule. In some embodiments, the methods described herein are used to detect and/or quantified multiple target nucleic acid molecules. The methods described herein can analyzed at least 1; 2; 3; 4; 5; 10; 20; 50; 100; 200; 500; 1,000; 2,000; 5,000; 10,000, 20,000; 50,000; 100,000; 200,000; 300,000; 400,000; 500,000; 600,000; 700,000; 800,000; 900,000; 1,000,000; 2,000,000 or 3,000,000 different target nucleic acids.

In some embodiments, the methods described herein are used to distinguish between target nucleic acids that differ from another nucleic acid by 1 nt. In some embodiments, the methods described herein are used to distinguish between target nucleic acids that differ from another nucleic acid by 1 nt or more than 1, 2, 3, 5, 10, 15, 20, 21, 22, 24, 25, 30 nt.

In some embodiments, the methods described herein are used to detect and/or quantify genomic DNA regions. In some embodiments, the methods described herein can discriminate and quantitate genomic DNA regions. The methods described herein can discriminate and quantitate at least 1; 2; 3; 4; 5; 10; 20; 50; 100; 200; 500; 1,000; 2,000; 5,000; 10,000, 20,000; 50,000; 100,000; 200,000; 300,000; 400,000; 500,000; 600,000; 700,000; 800,000; 900,000; 1,000,000; 2,000,000 or 3,000,000 different genomic DNA regions. The methods described herein can discriminate and quantitate genomic DNA regions varying by 1 nt or more than 1, 2, 3, 5, 10, 15, 20, 21, 22, 24, 25, 30 nt.

In some embodiments, the methods described herein are used to detect and/or quantify genomic DNA regions such as a region containing a DNA polymorphism. A polymorphism refers to the occurrence of two or more genetically determined alternative sequences or alleles in a population. A polymorphic marker or site is the locus at which divergence occurs. Preferred markers have at least two alleles, each occurring at a frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include single nucleotide polymorphisms (SNP's), restriction fragment length polymorphisms (RFLP's), short tandem repeats (STRs), variable number of tandem repeats (VNTR's), hypervariable regions, minisatellites, dinucleotide repeats, trinucleotide repeats, tetranucleotide repeats, simple sequence repeats, and insertion elements such as Alu. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens. In some embodiments, the methods described herein can discriminate and quantitate a DNA region containing a DNA polymorphism. The methods described herein can discriminate and quantitate of at least 1; 2; 3; 4; 5; 10, 20; 50; 100; 200; 500; 1,000; 2,000; 5,000; 10,000, 20,000; 50,000; 100,000; 200,000; 300,000; 400,000; 500,000; 600,000; 700,000; 800,000; 900,000; 1,000,000; 2,000,000 or 3,000,000 DNA polymorphism.

In some embodiments, the methods described herein can discriminate and quantitate at least 1; 2; 3; 4; 5; 10; 20; 50; 100; 200; 500; 1,000; 2,000; 5,000; 10,000, 20,000; 50,000; 100,000; 200,000; 300,000; 400,000; 500,000; 600,000; 700,000; 800,000; 900,000; 1,000,000; 2,000,000 or 3,000,000 different polymorphic markers.

In some embodiments, the methods described herein can discriminate and quantitate at least 1; 2; 3; 4; 5; 10; 20; 50; 100; 200; 500; 1,000; 2,000; 5,000; 10,000, 20,000; 50,000; 100,000; 200,000; 300,000; 400,000; 500,000; 600,000; 700,000; 800,000; 900,000; 1,000,000; 2,000,000 or 3,000,000 different SNPs.

In some embodiments, the methods described herein are used to detect and/or quantify gene expression. In some embodiments, the methods described herein provide high discriminative and quantitative analysis of multiples genes. The methods described herein can discriminate and quantitate the expression of at least 1, 2, 3, 4, 5, 10, 20, 50, 100, 200, 500, 1,000, 2,000, 5,000, 10,000, 20,000, 50,000, 100,000, different target nucleic acids.

In some embodiments, the methods described herein are used to detect and/or quantify gene expression of genes with similar sequences. The methods described herein can discriminate and quantitate the expression of genes varying by 1 nt or more than 1, 2, 3, 4, 5, 10, 12, 15, 20, 21, 22, 24, 25, 30 nt.

In some embodiments, the methods described herein are used to detect and/or quantify genomic DNA regions by mapping the region to the genome of a species in the case where the transplant donor and the transplant recipient are not from the same species (e.g., xenotransplants). In some embodiments, the methods described herein can discriminate and quantitate a DNA region from a species. The methods described herein can discriminate and quantitate of at least 1; 2; 3; 4; 5; 10; 20; 50; 100; 200; 500; 1,000; 2,000; 5,000; 10,000, 20,000; 50,000; 100,000; 200,000; 300,000; 400,000; 500,000; 600,000; 700,000; 800,000; 900,000; 1,000,000; 2,000,000 or 3,000,000 DNA regions from a species.

In some embodiments, the methods described herein are used for diagnosing or predicting transplant status or outcome (e.g. transplant rejection). In some embodiments, the methods described herein are used to detect and/or quantify target nucleic acids to determine whether a patient or subject is displaying transplant tolerance. In some embodiments, the methods described herein are used to detect and/or quantify target nucleic acids for diagnosis or prediction of transplant rejection. In some embodiments, the methods described herein are used to detect and/or quantify target nucleic acids for determining an immunosuppressive regimen for a subject who has received a transplant, e.g., an allograft. In some embodiments, the methods described herein are used to detect and/or quantify target nucleic acids to predict transplant survival in a subject that have received a transplant. The invention provides methods of diagnosing or predicting whether a transplant in a transplant patient or subject will survive or be lost. In certain embodiments, the methods described herein are used to detect and/or quantify target nucleic acids to diagnose or predict the presence of long-term graft survival. In some embodiments, the methods described herein are used to detect and/or quantify target nucleic acids for diagnosis or prediction of non-rejection based transplant injury. Examples of non-rejection based graft injury include, but are not limited to, ischemic injury, virus infection, peri-operative ischemia, reperfusion injury, hypertension, physiological stress, injuries due to reactive oxygen species and injuries caused by pharmaceutical agents.

As used herein the term "diagnose" or "diagnosis" of a transplant status or outcome includes predicting or diagnosing the transplant status or outcome, determining predisposition to a transplant status or outcome, monitoring treatment of transplant patient, diagnosing a therapeutic response of transplant patient, and prognosis of transplant status or outcome, transplant progression, and response to particular treatment.

Donor Organ Nucleic Acid Detection and Analysis

In some embodiments, the methods, devices, compositions and kits are used to establish a genotype for both the donor and the recipient before transplantation to enable the detection of donor-specific nucleic acids such as DNA or RNA in bodily fluids such as blood or urine from the organ recipient after transplantation. This approach allows for a reliable identification of sequences arising solely from the organ transplantation that can be made in a manner that is independent of the genders of donor and recipient.

In some embodiments, a genetic fingerprint is generated for the donor organ. Both the donor and recipient will be genotyped prior to transplantation. Genotyping of transplant donors and transplant recipients establishes a profile, using distinguishable markers, for detecting donor nucleic acids (e.g. circulating cell-free nucleic acid or nucleic acids from circulating donor cells). In some embodiments, for xenotransplants, nucleic acids from the donors can be mapped to the genome of the donor species.

Following transplantation, samples as described above can be drawn from the patient and analyzed for markers. The proportion of donor nucleic acids can be monitored over time and an increase in this proportion can be used to determine transplant status or outcome (e.g. transplant rejection).

In some embodiments, genotyping comprises detection and quantitation of nucleic acids from circulating transplant donor cells or circulating cell-free nucleic acids. Examples of nucleic acids include, but are not limited to double-stranded DNA, single-stranded DNA, single-stranded DNA hairpins, DNA/RNA hybrids, RNA (e.g. mRNA or miRNA) and RNA hairpins. In some embodiments, the nucleic acid is DNA. In some embodiments, the nucleic acid is RNA. For instance, cell-free RNA is also present in human plasma (Tong, Y. K. Lo, Y. M., Clin Chim Acta, 363, 187-196 (2006)) and cDNA sequencing of organ-specific transcripts provides another option to detect donor-specific nucleic acids arising from cells in the transplanted organ. In some embodiments, nucleic acids collected from circulating cells in the blood are used.

In some embodiments, genotyping comprises detection and quantitation of polymorphic markers. Examples of polymorphic markers include single nucleotide polymorphisms (SNP's), restriction fragment length polymorphisms (RFLP's), variable number of tandem repeats (VNTR's), short tandem repeats (STRs), hypervariable regions, minisatellites, dinucleotide repeats, trinucleotide repeats, tetranucleotide repeats, simple sequence repeats, and insertion elements such as Alu. In some embodiments, genotyping comprises detection and quantitation of STRs. In some embodiments, genotyping comprises detection and quantitation of VNTRs.

In some embodiments, genotyping comprises detection and quantitation of SNPs. Without intending to be limited to any theory, any donor and recipient will vary at roughly three million SNP positions if fully genotyped. Usable SNPs must be homozygous for the recipient and ideally homozygous for the donor as well. While the majority of these positions will contain SNPs that are heterozygous for either the donor or the recipient, over 10% (or hundreds of thousands) will be homozygous for both donor and recipient meaning a direct read of that SNP position can distinguish donor DNA from recipient DNA. For example, after genotyping a transplant donor and transplant recipient, using existing genotyping platforms know in the art including the one described herein, one could identify approximately 1.2 million total variations between a transplant donor and transplant recipient. Usable SNPs may comprise approximately 500,000 heterozygous donor SNPs and approximately 160,000 homozygous donor SNPs. Companies (such as Applied Biosystems, Inc.) currently offer both standard and custom-designed TaqMan probe sets for SNP genotyping that can in principle target any desired SNP position for a PCR-based assay (Livak, K. L., Marmaro, J., Todd, J. A., Nature Genetics, 9, 341-342 (1995); De La Vefa, F. M., Lazaruk, K. D., Rhodes, M. D., Wenz, M. H., Mutation Research, 573, 111-135 (2005)). With such a large pool of potential SNPs to choose from, a usable subset of existing or custom probes can be selected to serve as the probe set for any donor/recipient pair. In some embodiments, digital PCR or real-time PCR performed on the nucleic acids recovered from plasma or other biological samples will directly quantitate the percentage of donor-specific species seen in the sample. In some embodiments, sequencing performed on the nucleic acid recovered from plasma or other biological samples will directly quantitate the percentage of donor-specific species seen in the sample. In some embodiments, arrays can be used on the nucleic acids recovered from plasma or other biological samples to directly quantitate the percentage of donor-specific species seen in the sample.

Due to the low number of expected reads for any individual nucleic acid (e.g. SNP) in patient samples, some preamplification of the sample material may be required before analysis to increase signal levels, but using either preamplification, sampling more target nucleic acid positions (e.g. SNP positions), or both, will provide a reliable read-out of the transplant donor nucleic acid fraction. Preamplification can be preformed using any suitable method known in the art such as multiple displacement amplification (MDA) (Gonzalez et al. Envircon Microbiol; 7(7); 1024-8 (2005)) or amplification with outer primers in a nested PCR approach. This permits detection and analysis of donor nucleic acids even if the total amount of donor nucleic acid in the sample (e.g. blood from transplant patient) is only up to 1 µg, 500 ng, 200 ng, 100 ng, 50 ng, 40 ng, 30 ng, 20 ng, 10 ng, 5 ng, 1 ng, 500 pg, 200 pg, 100 pg, 50 pg, 40 pg, 30 pg, 20 p, 10 pg, 5 pg, or 1 pg or between 15 µg, 510 µg, or 1050 µg.

a. PCR

Genotyping donor and recipient nucleic acids, and/or detection, identification and/or quantitation of the donor-specific nucleic acids after transplantation (e.g. polymorphic markers such as SNPs) can be performed by PCR. Examples of PCR techniques that can be used to detect, identify and/or quantitate the donor-specific nucleic acids include, but are not limited, to quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that may be used to amplify specific polymorphic loci include those described in, U.S. Pat. Nos. 5,242,794, 5,494,810, 4,988,617 and 6,582,938. In some embodiments, Detection, identification and/or quantitation of the donor-specific nucleic acids (e.g. polymorphic markers such as SNPs) is performed by real-time PCR.

In some embodiments, digital PCR or real time PCR to quantitate the presence of specific polymorphisms that have already been identified in the initial genotyping step pre-transplantation. Compared with the quantitative PCR techniques used in some of the earlier cited work, digital PCR is a much more accurate and reliable method to quantitate nucleic acid species including rare nucleic acid species, and does not require a specific gender relationship between donor and recipient. (Warren, L., Bryder, D., Weissman, I. L., Quake, S. R., Proc Natl Acad Sci, 103, 17807-17812 (2006)). In some embodiments, digital PCR or real-time PCR assays can be used to quantitate the fraction of donor DNA in a transplant patient using probes targeted to several SNPs.

b. Sequencing

Genotyping donor and recipient nucleic acids, and/or detection, identification and/or quantitation of the donor-specific nucleic acids after transplantation (e.g. polymorphic markers such as SNPs) can be performed by sequencing such as whole genome sequencing or exome sequencing. Sequencing can be accomplished through classic Sanger sequencing methods which are well known in the art. Sequence can also be accomplished using high-throughput systems some of which allow detection of a sequenced nucleotide immediately after or upon its incorporation into a growing strand, i.e., detection of sequence in red time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read. Sequencing can be preformed using nucleic acids described herein such as genomic DNA, cDNA derived from RNA transcripts or RNA as a template.

In some embodiments, high-throughput sequencing involves the use of technology available by Helicos BioSciences Corporation (Cambridge, Mass.) such as the Single Molecule Sequencing by Synthesis (SMSS) method. SMSS is unique because it allows for sequencing the entire human genome with no pre amplification step needed. Thus, distortion and nonlinearity in the measurement of nucleic acids are reduced. This sequencing method also allows for detection of a SNP nucleotide in a sequence in substantially real time or real time. Finally, as mentioned above, SMSS is powerful because, like the MIP technology, it does not require a pre amplification step prior to hybridization. In fact, SMSS does not require any amplification. SMSS is described in part in US Publication Application Nos. 2006002471 I; 20060024678; 20060012793; 20060012784; and 20050100932.

In some embodiments, high-throughput sequencing involves the use of technology available by 454 Life-sciences, Inc. (Branford, Conn.) such as the Pico Titer Plate device which includes a fiber optic plate that transmits chemiluninescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density pricolitre reactors", Nature, doi: 10.1038/nature03959; and well as in US Publication Application Nos. 200200 12930; 20030058629; 20030 1001 02; 20030 148344; 20040248 161; 200500795 10,20050 124022; and 20060078909.

In some embodiments, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 200401061 30; 20030064398; 20030022207; and Constans, A., The Scientist 2003, 17(13):36.

In some embodiments of this aspect, high-throughput sequencing of RNA or DNA can take place using Any-Dot.chips (Genovoxx, Germany), which allows for the monitoring of biological processes (e.g., miRNA expression or allele variability (SNP detection). In particular, the Any-Dot-chips allow for 10x-50x enhancement of nucleotide fluorescence signal detection. AnyDot.chips and methods for using them are described in part in International Publication Application Nos. WO 02088382, WO 03020968, WO 0303 1947, WO 2005044836, PCTEP 05105657, PCMEP 05105655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al, Science 24 Mar. 2000; and M. J, Levene, et al. Science 299:682-686, January 2003; as well as US Publication Application No. 20030044781 and 2006/0078937. Overall such system involve sequencing a target nucleic acid molecule having a plurality of bases by the temporal addition of bases via a polymerization reaction that is measured on a molecule of nucleic acid, i e., the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable lo move along the target nucleic acid molecule and extend the oligonucleotide primer at an active site. A plurality of labeled types of nucleotide analogs are provided proximate to the active site, with each distinguishably type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

In some embodiments, shotgun sequencing is performed. In shotgun sequencing, DNA is broken up randomly into numerous small segments, which are sequenced using the chain termination method to obtain reads. Multiple overlapping reads for the target DNA are obtained by performing several rounds of this fragmentation and sequencing. Computer programs then use the overlapping ends of different reads to assemble them into a continuous sequence In some embodiments, the invention provides methods for detection and quantitation of SNPs using sequencing. In this case, one can estimate the sensitivity of detection. There are two components to sensitivity: (i) the number of molecules analyzed (depth of sequencing) and (ii) the error rate of the sequencing process. Regarding the depth of sequencing, a frequent estimate for the variation between individuals is that about one base per thousand differs. Currently, sequencers such as the Illumina Genome Analyzer have read lengths exceeding 36 base pairs. Without intending to be limited to any theory or specific embodiment, this means that roughly one in 30 molecules analyzed will have a potential SNP. While the fraction of donor DNA in the recipient blood is currently not well determined and will depend on organ type, one can take 1% as a baseline estimate based on the literature and applicants own studies with heart transplant patients. At this fraction of donor DNA, approximately one in 3,000 molecules analyzed will be from the donor and informative about donor genotype. On the Genome Analyzer one can obtain about 10 million molecules per analysis channel and there are 8 analysis channels per instrument run. Therefore, if one sample is loaded per channel, one should be able to detect about 3,000 molecules that can be identified as from the donor in origin, more than enough to make a precise determination of the fraction of donor DNA using the above parameters. If one wants to establish a lower limit of sensitivity for this method by requiring at least 100 donor molecules to be detected, then it should have a sensitivity capable of detecting donor molecules when the donor fraction is as low as 0.03%. Higher sensitivity can be achieved simply by sequencing more molecules, i.e. using more channels.

The sequencing error rate also affects the sensitivity of this technique. For an average error rate of $\varepsilon$, the chance of a single SNP being accidentally identified as of donor origin as a result of a mis-read is roughly $\varepsilon/3$. For each individual read, this establishes a lower limit of sensitivity of one's ability to determine whether the read is due to donor or recipient. Typical sequencing error rates for base substitutions vary between platforms, but are between 0.5-1.5%. This places a potential limit on sensitivity of 0.16 to 0.50%. However, it is possible to systematically lower the sequencing error rate by resequencing the sample template multiple times, as has been demonstrated by Helicos BioSciences (Harris, T. D., et al., Science, 320, 106-109 (2008)). A single application of resequencing would reduce the expected error rate of donor SNP detection to $\varepsilon^2/9$ or less than 0.003%.

Figure 5:
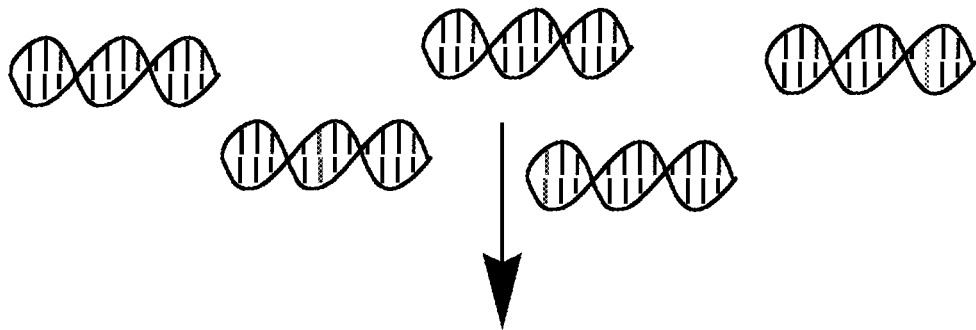
FIG. 5 depicts in one embodiments of the invention a general strategy to monitor all transplant patients

FIG. 5 shows in one embodiments of the inventions a general strategy for monitor all patients, (i.e., not just female patients receiving male organs), to determine a transplants status or outcome. Genotyping of donor and recipient can establish a single nucleotide polymorphism (SNP) profile for detecting donor DNA. Shotgun sequencing of cell-free DNA in plasma, with analysis of observed unique SNPs, allows quantitation of % donor DNA. While any single SNP may be difficult to detect with so little DNA in plasma, with hundred of thousands or more signals to consider, high sensitivity should be possible.

c. Arrays

Genotyping donor and recipient nucleic acids, and/or detection, identification and/or quantitation of the donor-specific nucleic acids after transplantation (e.g. polymorphic markers such as SNPs) can be performed using arrays (e.g. SNPs arrays). Results can be visualized using a scanner that enables the viewing of intensity of data collected and software to detect and quantify nucleic acid. Such methods are disclosed in part U.S. Pat. No. 6,505,125. Another method contemplated by the present invention to detect and quantify nucleic acids involves the use of bead as is commercially available by Illumina, Inc. (San Diego) and as described in U.S. Pat. Nos. 7,035,740; 7,033,754; 7,025,935, 6,998,274; 6,942,968; 6,913,884; 6,890,764; 6,890,741; 6,858,394; 6,812,005; 6,770,441; 6,620,584; G,544,732; 6,429,027; 6,396,995; 6,355,431 and US Publication Application Nos. 20060019258; 0050266432; 20050244870; 20050216207; 20050181394; 20050164246; 20040224353; 20040185482; 20030198573; 20030175773; 20030003490; 20020187515; and 20020177141; and in B. E. Stranger, et al., Public Library of Science-Genetics, I (6), December 2005; Jingli Cai, el al., Stem Cells, published online Nov. 17, 2005; C. M. Schwartz, et al., Stem Cells and Development, f 4, 517-534, 2005; Barnes, M., J. el al., Nucleic Acids Research, 33 (181, 5914-5923, October 2005; and Bibikova M, et al. Clinical Chemistry, Volume 50, No. 12, 2384-2386, December 2004. Additional description for preparing RNA for bead arrays is described in Kacharmina J E, et al., Methods Enzymol303: 3-18, 1999; Pabon C, et al., Biotechniques 31(4): 8769, 2001; Van Gelder R N, et a]., Proc Natl Acad Sci USA 87: 1663-7 (1990); and Murray, SS. BMC Genetics B(SuppII):SX5 (2005).

When analyzing SNP according to the methods described herein, the transplant donor and/or recipient nucleic acids can be labeled and hybridized with a DNA microarray (e.g., 100K Set Array or other array). Results can be visualized using a scanner that enables the viewing of intensity of data collected and software "calls" the SNP present at each of the positions analyzed. Computer implemented methods for determining genotype using data h m mapping arrays are disclosed, for example, in Liu, et al., Bioinformatics 19:2397-2403, 2003; and Di et al., Bioinformatics 21: 1958-63, 2005. Computer implemented methods for linkage analysis using mapping array data are disclosed, for example, in Ruschendorf and Nusnberg, Bioinfonnatics 21:2123-5,2005; and Leykin et a]., BMC Genet. 6:7, 2005; and in U.S. Pat. No. 5,733,729.

In some embodiments of this aspect, genotyping microarrays that are used to detect SNPs can be used in combination with molecular inversion probes (MIPS) as described in Hardenbol et al., Genome Res. 15(2):269-275,2005, Hardenbol, P. et al. Nature Biotechnology 21 (6), 673-8, 2003; Faham M, et al. Hum Mol Genet. August 1; 10(16): 1657-64, 2001: Maneesh Jain, Ph.D., et al. Genetic Engineering News V24: No. 18, 2004; and Fakhrai-Rad H, el al. Genome Res. July; 14(7):1404-12, 2004; and in U.S. Pat. No. 5,858,412. Universal tag arrays and reagent kits for performing such locus specific genotyping using panels of custom M1Ps are available from Affymetrix and ParAllele. MIP technology involves the use enzymological reactions that can score up to 10,000: 20,000, 50,000; 100,000; 200,000; 500,000; 1,000,000; 2,000,000 or 5,000,000 SNPs (target nucleic acids) in a single assay. The enzymological reactions are insensitive to crossreactivity among multiple probe molecules and there is no need for pre-amplification prior to hybridization of the probe with the genomic DNA. In any of the embodiments, the target nucleic acid(s) or SNPs can be obtained from a single cell.

Another method contemplated by the present invention to detect target nucleic acids involves the use of bead arrays (e.g., such as one commercially available by Illumina, Inc.) as described in U.S. Pat. Nos. 7,040,959; 7,035,740; 7,033,754; 7,025,935, 6,998,274; 6,942,968; 6,913,884; 6,890,764; 6,890,741; 6,858,394; 6,846,460; 6,812,005; 6,770,441; 6,663,832; 5,520,584; 6,544,732; 6,429,027; 6,396,995; 6,355,431 m d US Publication Application Nos. 20060019258; 20050266432; 20050244870; 20050216207; 20050181394; 20050164246; 20040224353; 20040185482; 20030198573; 200301 75773; 20030003490; 200201 8751 5; and 20020177141; as well as Shen, R., et al. Mutation Research 573 70-82 (2005).

d. Other Techniques

In some of the embodiment herein, nucleic acids are quantified. Methods for quantifying nucleic acids are known in the art and include, but are not limited to, gas chromatography, supercritical fluid chromatography, liquid chromatography (including partition chromatography, adsorption chromatography, ion exchange chromatography, size exclusion chromatography, thin-layer chromatography, and affinity chromatography), electrophoresis (including capillary electrophoresis, capillary zone electrophoresis, capillary isoelectric focusing, capillary electrochromatography, micellar electrokinetic capillary chromatography, isotachophoresis, transient isotachophoresis and capillary gel electrophoresis), comparative genomic hybridization (CGH), microarrays, bead arrays, and high-throughput genotyping such as with the use of molecular inversion probe (MIP).

Another method contemplated by the present invention to detect and/or quantify target nucleic acids involves the use of nanoreporters as described in U.S. Pat. No. 7,473,767 entitled "Methods for detection and quantification of analytes in complex mixtures", US patent publication no. 2007/0166708 entitled "Methods for detection and quantification of analytes in complex mixtures", U.S. application Ser. No. 11/645,270 entitled "Compositions comprising oriented, immobilized macromolecules and methods for their preparation", PCT application no U.S. Ser. No. 06/049,274 entitled "Nanoreporters and methods of manufacturing and use thereof", Quantification of target nucleic acid can be used to determine the percentage of donor nucleic acids such as DNA.

e. Labels

Detection and/or quantification of target nucleic acids can be done using fluorescent dyes known in the art. Fluorescent dyes may typically be divided into families, such as fluorescein and its derivatives; rhodamine and its derivatives; cyanine and its derivatives; coumarin and its derivatives; Cascade Blue™ and its derivatives; *Lucifer* Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa Fluor®-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine™) carboxy tetramethylrhodamine (TAMRA™), carboxy-X-rhodamine (ROX™), LIZ™, VIC™, NED™, PET™., SYBR, PicoGreen, RiboGreen, and the like. Descriptions of fluorophores and their use, can be found in, among other places, R. Haugland, Handbook of Fluorescent Probes and Research Products, 9.sup.th ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, Va. Near-infrared dyes are expressly within the intended meaning of the terms fluorophore and fluorescent reporter group.

In another aspect of the invention, a branched-DNA (bDNA) approach is used to increase the detection sensitivity. In some embodiments, bDNA approach is applied to an array detection assay. The array detection assay can be any array assay known in the art, including the array assays described herein. bDNA approach amplifies the signals through a branched DNA that are attached by tens or hundreds of alkaline phosphatase molecules. Thus, the signals are significantly amplified while the fidelity of the original nucleic acid target abundance is maintained.

Methods

In one aspect the invention provides methods for the diagnosis or prediction of transplant status or outcome in a subject who has received a transplant. The transplant status or outcome may comprise rejection, tolerance, non-rejection based transplant injury, transplant function, transplant survival, chronic transplant injury, or titer pharmacological immunosuppression. Examples of non-rejection based allograft injury include, but are not limited to, ischemic injury, virus infection, peri-operative ischemia, reperfusion injury, hypertension, physiological stress, injuries due to reactive oxygen species and injuries caused by pharmaceutical agents. The transplant status or outcome may comprise vascular complications or neoplastic involvement of the transplanted organ.

In some embodiments, the invention provides methods of diagnosing or predicting transplant status or outcome comprising the steps of: (i) providing a sample from a subject who has received a transplant from a donor; (ii) determining the presence or absence of one or more nucleic acids from the donor transplant, wherein the one or more nucleic acids from the donor are identified based on a predetermined marker profile; and (iii) diagnosing or predicting transplant status or outcome based on the presence or absence of the one or more nucleic acids from said donor.

In some embodiments, the methods of the invention are used to establish a genotype for both the donor and the recipient before transplantation. In some embodiments, the genotyping of both the donor and the recipient before transplantation enables the detection of donor-specific nucleic acids such as DNA or RNA in bodily fluids as described herein (e.g., blood or urine) from the organ recipient after transplantation. In some embodiments a marker profile for the donor is determined based on the genotyping of the transplant donor. In some embodiments, a marker profile is determined for the transplant recipient based on the genotyping of the transplant recipient. In some embodiments, a marker profile is established by selecting markers that are distinguishable between the transplant donor and the subject receiving the transplant. This approach allows for a reliable identification of nucleic acids arising solely from the organ transplantation that can be made in a manner that is independent of the genders of donor and recipient.

Genotyping of the transplant donor and/or the transplant recipient may be performed by any suitable method known in the art including those described herein such as sequencing, nucleic acid array or PCR. In some embodiments, genotyping of the transplant donor and/or the transplant recipient is performed by shotgun sequencing. In some embodiments, genotyping of the transplant donor and/or the transplant recipient is performed using a DNA array. In some embodiments, genotyping of the transplant donor and/or the transplant recipient is performed using a polymorphism array such as a SNP array.

In some embodiments, the marker profile is a polymorphic marker profile. Polymorphic marker profile may comprise one or more single nucleotide polymorphisms (SNP's), one or more restriction fragment length polymorphisms (RFLP's), one or more short tandem repeats (STRs) or more variable number of tandem repeats (VNTR's), one or more hypervariable regions, one or more minisatellites, one or more dinucleotide repeats, one or more trinucleotide repeats, one or more tetranucleotide repeats, one or more simple sequence repeats, or one or more insertion elements. In some embodiments, the marker profile comprises at least 1; 2; 3; 4; 5; 10; 20; 50; 100; 200; 500; 1,000; 2,000; 5,000; 10,000; 20,000; 50,000; 100,000; 200,000; 300,000; 400,000; 500,000; 600,000; 700,000; 800,000; 900,000; 1,000,000; 2,000,000 or 3,000,000 different polymorphic markers.

In some embodiments, the polymorphic marker profile comprises one or more SNPs. In some embodiments, the marker profile comprises at least 1; 2; 3; 4; 5; 10; 20; 50; 100; 200; 500; 1,000; 2,000; 5,000; 10,000; 20,000; 50,000; 100,000; 200,000; 300,000; 400,000; 500,000; 600,000; 700,000; 800,000; 900,000; 1,000,000; 2,000,000 or 3,000,000 different SNPs.

Following transplantation, samples as described above can be drawn from the patient and analyzed for the presence or absence of one or more nucleic acids from the transplant donor. In some embodiments, the sample is blood, plasma, serum or urine. The proportion and/or amount of donor nucleic acids can be monitored over time and an increase in this proportion can be used to determine transplant status or outcome (e.g. transplant rejection).

The presence or absence of one or more nucleic acids from the transplant donor in the transplant recipient may be determined by any suitable method known in the art including those described herein such as sequencing, nucleic acid arrays or PCR. In some embodiments, the presence or absence of one or more nucleic acids from the transplant donor in the transplant recipient is determined by shotgun sequencing. In some embodiments, the presence or absence of one or more nucleic acids from the transplant donor in the transplant recipient is determined using a DNA array. In some embodiments, the presence or absence of one or more nucleic acids from the transplant donor in the transplant recipient is determined using a polymorphism array such as a SNP array.

In some embodiments, where the transplant is a xenotransplant, detection, identification and/or quantitation of the donor-specific markers can be performed by mapping one or more nucleic acids (e.g., DNA) to the genome of the specie use to determine whether the one or more nucleic acids come from the transplant donor. Polymorphic markers as described above can also be used where the transplant is a xenotransplant.

In some embodiments, the presence or absence of circulating DNA or RNA from a transplant donor in a transplant recipient is used to determine the transplant status or outcome. The DNA can be double-stranded DNA, single-stranded DNA, single-stranded DNA hairpins, or cDNA. The RNA can be single stranded RNA or RNA hairpins. In some embodiments, the presence or absence of circulating DNA/RNA hybrids from a transplant donor in a transplant recipient is used to determine the transplant status or outcome. In some embodiments, the presence or absence of circulating mRNA from a transplant donor in a transplant recipient is used to determine the transplant status or outcome. In some embodiments, the presence or absence of circulating DNA from a transplant donor in a transplant recipient is used to determine the transplant status or outcome. In some embodiments, cDNA is used to determine the transplant status or outcome. The DNA or RNA can be obtained from circulating donor cells. Alternative, the DNA or RNA can be circulating cell-free DNA or circulating cell-free RNA In any of the embodiments described herein, the transplant graft maybe any solid organ and skin transplant. Examples of transplants, whose transplant status or outcome could be determined by the methods described herein, include but are not limited to, kidney transplant, heart transplant, liver transplant, pancreas transplant, lung transplant, intestine transplant and skin transplant.

In some embodiments, the invention provides methods of determining whether a patient or subject is displaying transplant tolerance. In some embodiments the invention provides methods for diagnosis or prediction of transplant rejection. The term "transplant rejection" encompasses both acute and chronic transplant rejection. In some embodiments, the invention further includes methods for determining an immunosuppressive regimen for a subject who has received a transplant, e.g., an allograft. In some embodiments, the invention further includes methods for determining the effectiveness of an immunosuppressive regimen for a subject who has received a transplant. Certain embodiments of the invention provide methods of predicting transplant survival in a subject that has received a transplant. The invention provides methods of diagnosing or predicting whether a transplant in a transplant patient or subject will survive or be lost. In certain embodiments, the invention provides methods of diagnosing or predicting the presence of long-term graft survival. In some embodiments, the invention provides methods for diagnosis or prediction of non-rejection based transplant injury. Examples of non-rejection based graft injury include, but are not limited to, ischemic injury, virus infection, pen-operative ischemia, reperfusion injury, hypertension, physiological stress, injuries due to reactive oxygen species and injuries caused by pharmaceutical agents. In some embodiments, the invention provides methods for diagnosis or prediction of vascular complications or neoplastic involvement of the transplanted organ.

In some embodiments, the amount of one or more nucleic acids from the transplant donor in a sample from the transplant recipient is used to determine the transplant status or outcome. Thus, in some embodiments, the methods of the invention further comprise quantitating the one or more nucleic acids from the transplant donor. In some embodiments, the amount of one or more nucleic acids from the donor sample is determined as a percentage of total the nucleic acids in the sample. In some embodiments, the amount of one or more nucleic acids from the donor sample is determined as a ratio of the total nucleic acids in the sample. In some embodiments, the amount of one or more nucleic acids from the donor sample is determined as a ratio or percentage compared to one or more reference nucleic acids in the sample. For instance, the amount of one or more nucleic acids from the transplant donor can be determined to be 10% of the total nucleic acids in the sample. Alternatively, the amount of one or more nucleic acids from the transplant donor can be at a ratio of 1:10 compared to total nucleic acids in the sample. Further, the amount of one or more nucleic acids from the transplant donor can be determined to be 10% or at a ratio of 1:10 of a reference gene such a β-globin. In some embodiments, the amount of one or more nucleic acids from the transplant donor can be determined as a concentration. For example, the amount of one or more nucleic acids from the donor sample can be determined to be 1 ug/mL.

In some embodiments, the amount of one or more nucleic acids from the transplant donor above a predetermined threshold value is indicative of a transplant status or outcome. For example, the normative values for clinically stable post-transplantation patients with no evidence of graft rejection or other pathologies can be determined. An increase in the amount of one or more nucleic acids from the transplant donor above the normative values for clinically stable post-transplantation patients could indicate a change in transplant status or outcome such as transplant rejection or transplant injury. On the other hand, an amount of one or more nucleic acids from the transplant donor below or at the normative values for clinically stable post-transplantation patients could indicate graft tolerance or graft survival.

In some embodiments, different predetermined threshold values are indicative of different transplant outcomes or status. For example, as discussed above, an increase in the amount of one or more nucleic acids from the transplant donor above the normative values for clinically stable post-transplantation patients could indicate a change in transplant status or outcome such as transplant rejection or transplant injury. However, an increase in the amount of one or more nucleic acids from the transplant donor above the normative values for clinically stable post-transplantation patients but below a predetermined threshold level could indicate a less serious condition such as a viral infection rather than transplant rejection. An increase in the amount of one or more nucleic acids from the transplant donor above a higher threshold could indicate transplant rejection.

In some embodiments, temporal differences in the amount of said one or more nucleic acids from the transplant donor are indicative of a transplant status or outcome. For instance, a transplant patient can be monitored over time to determine the amount of one or more nucleic acids from the transplant donor. A temporary increase in the amount of one or more nucleic acids from the transplant donor, which subsequently return to normal values, might indicate a less serious condition rather than transplant rejection. On the other hand, a sustained increase in the amount one or more nucleic acids from the transplant donor might indicate a serious condition such as transplant rejection.

In some embodiments, temporal differences in the amount of said one or more nucleic acids from the transplant donor can be used to monitor effectiveness of an immunosuppressant treatment or to select an immunosuppressant treatment. For instance, the amount of one or more nucleic acids from the transplant donor can be determined before and after an immunosuppressant treatment. A decrease in the one or more nucleic acids from the transplant donor after treatment may indicate that the treatment was successful in preventing transplant rejection. Additionally, the amount of one or more nucleic acids from the transplant donor can be used to choose between immunosuppressant treatments, for examples, immunosuppressant treatments of different strengths. For example, a higher amount in one or more nucleic acids from the transplant donor may indicate that there is a need of a very potent immunosuppressant, whereas a lower amount in one or more nucleic acids from the transplant donor may indicate that a less potent immunosuppressant may be used.

The invention provides methods that sensitive and specific. In some embodiments, the methods described herein for diagnosing or predicting transplant status or outcome have at least 56%, 60%, 70%, 80%, 90%, 95% or 100% sensitivity. In some embodiments, the methods described herein have at least 56% sensitivity. In some embodiments, the methods described herein have at least 78% sensitivity. In some embodiments, the methods described herein have a specificity of about 70% to about 100%. In some embodiments, the methods described herein have a specificity of about 80% to about 100%. In some embodiments, the methods described herein have a specificity of about 90% to about 100%. In some embodiments, the methods described herein have a specificity of about 100%.

Also provided herein are methods for screening and identifying markers recognizing a donor nucleic acid that can be useful in the methods described herein, e.g. diagnosing or predicting transplant status or outcome. In some embodiments, the donor nucleic acid is cell-free DNA or DNA isolated from circulating donor cells.

Donor nucleic acid can be identified by the methods described herein including the methods described in the Examples. After identifying these, then one could look at the donor nucleic acids and examine them for their correlation with transplant status and outcomes such as chronic graft injury, rejection, and tolerance. In some embodiments, the longitudinal change of donor nucleic acids is studied. If clinically significant, these levels could be followed to titer pharmacological immunosuppression, or could be studied as a target for depletion.

Kits

Also provided are reagents and kits thereof for practicing one or more of the above-described methods. The subject reagents and kits thereof may vary greatly. Reagents of interest include reagents specifically designed for use in production of the above-described: (i) genotyping of a transplant donor and a transplant recipient; (ii) identification of marker profiles; and (ii) detection and/or quantitation of one or more nucleic acids from a transplant donor in a sample obtained from a transplant recipient.

One type of such reagents are one or more probes or an array of probes to genotype and/or to detect and/or to quantitate one or more nucleic acids. A variety of different array formats are known in the art, with a wide variety of different probe structures, substrate compositions and attachment technologies.

The kits of the subject invention may include the above-described arrays. Such kits may additionally comprise one or more therapeutic agents. The kit may further comprise a software package for data analysis, which may include reference profiles for comparison with the test profile.

The kits may comprise reagents such as buffers, and $H_2O$. The kits may comprise reagents necessary to perform nucleic acid extraction and/or nucleic acid detection using the methods described herein such as PCR and sequencing.

Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such kits may also include instructions to access a database. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

Computer Program

Any of the methods above can be performed by a computer program product that comprises a computer executable logic that is recorded on a computer readable medium. For example, the computer program can execute some or all of the following functions: (i) controlling isolation of nucleic acids from a sample, (ii) pre-amplifying nucleic acids from the sample, (iii) amplifying, sequencing or arraying specific polymorphic regions in the sample, (iv) identifying and quantifying a marker profile in the sample, (v) comparing data on marker profile detected from the sample with a predetermined threshold, (vi) determining a transplant status or outcome, (vi) declaring normal or abnormal transplant status or outcome. In particular, the computer executable logic can analyze data on the detection and quantity of polymorphism(s) (e.g. SNPs).

The computer executable logic can work in any computer that may be any of a variety of types of general-purpose computers such as a personal computer, network server, workstation, or other computer platform now or later developed. In some embodiments, a computer program product is described comprising a computer usable medium having the computer executable logic (computer software program, including program code) stored therein. The computer executable logic can be executed by a processor, causing the processor to perform functions described herein. In other embodiments, some functions are implemented primarily in hardware using, for example, a hardware state machine. Implementation of the hardware state machine so as to perform the functions described herein will be apparent to those skilled in the relevant arts.

The program can provide a method of evaluating a transplant status or outcome in a transplant recipient by accessing data that reflects the genotyping of the transplant donor and the transplant patient, and/or the presence or absence of one or more nucleic acids from the transplant donor in the circulation of the transplant patient post-transplantation.

In one embodiment, the computer executing the computer logic of the invention may also include a digital input device such as a scanner. The digital input device can provide information on a nucleic acid, e.g., polymorphism levels/quantity. For example, a scanner of this invention can provide an image of the polymorphism (e.g., SNPs) according to method herein. For instance, a scanner can provide an image by detecting fluorescent, radioactive, or other emission; by detecting transmitted, reflected, or scattered radiation; by detecting electromagnetic properties or other characteristics; or by other techniques. The data detected is typically stored in a memory device in the form of a data file.

In one embodiment, a scanner may identify one or more labeled targets. For instance, a first DNA polymorphism may be labeled with a first dye that fluoresces at a particular characteristic frequency, or narrow band of frequencies, in response to an excitation source of a particular frequency. A second DNA polymorphism may be labeled with a second dye that fluoresces at a different characteristic frequency. The excitation sources for the second dye may, but need not, have a different excitation frequency than the source that excites the first dye, e.g., the excitation sources could be the same, or different, lasers.

In some embodiments, the invention provides a computer readable medium comprising a set of instructions recorded thereon to cause a computer to perform the steps of (i) receiving data from one or more nucleic acids detected in a sample from a subject who has received transplant from a donor, wherein said one or more nucleic acids are nucleic acids from said donor transplant, and wherein said one or more nucleic acids from said donor are identified based on a predetermined marker profile; and (ii) diagnosing or predicting transplant status or outcome based on the presence or absence of the one or more nucleic acids.

EXAMPLES

Example 1: Detection of Donor DNA in Organ Transplant Recipients

Using digital PCR as described before (Warren, L., Bryder, D., Weissman, I. L., Quake, S. R., Proc Natl Acad Sci, 103, 17807-17812 (2006); Fan, H. C. Quake, S. R., Anal Chem, 79, 7576-7579 (2007)), the amount of chromosome Y and chromosome 1 markers were quantitated for female patients receiving either male or female hearts in plasma samples taken at the same time that an endomyocardial biopsy determined a grade 3A or 3B rejection episode.

While blood transfusions/male child birth are known mechanisms to have detectable cY signature in a female patient, FIG. 2 shows that the overall levels of cY are uniformly higher for patients receiving hearts from male donors. No significant chromosome Y signal from four control female-to-female transplant patients was detected. On the other hand, 1.5-8% total genomic fraction for chromosome Y signals was observed at the rejection time points for three male-to-female transplant patients across four rejection episodes.

Figure 3:
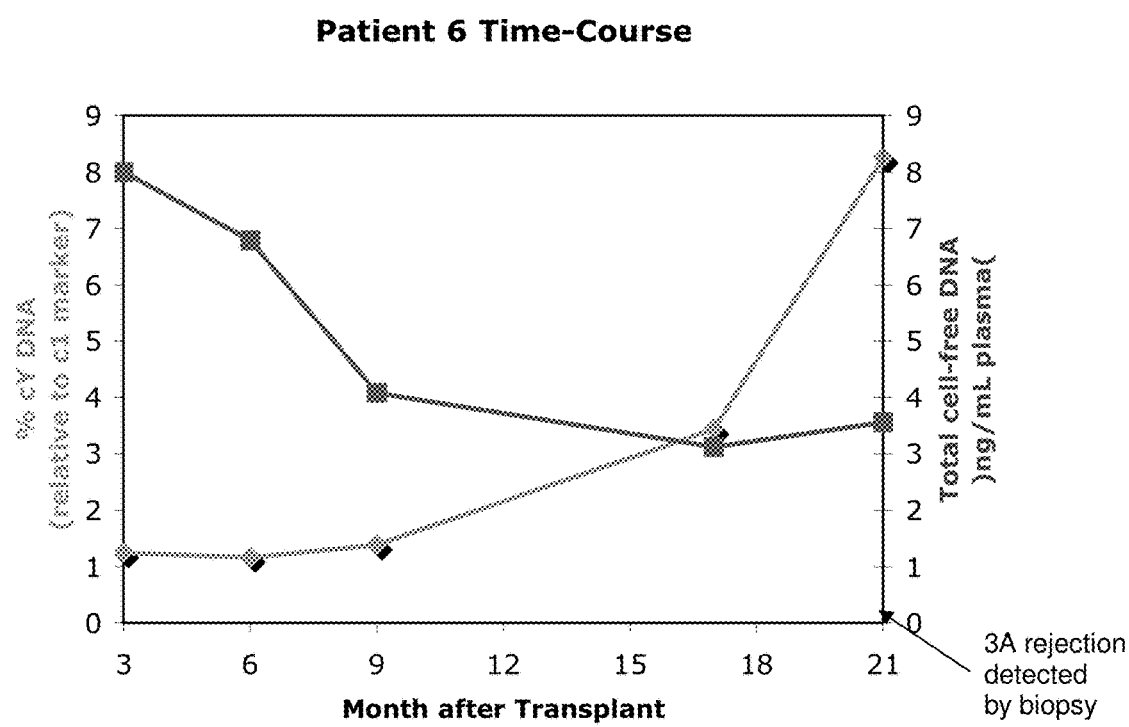
FIG. 3 shows a time course study for detection of donor DNA in a transplant patient that received a gender mismatched transplant and suffered a 3A rejection episode.
Figure 4:
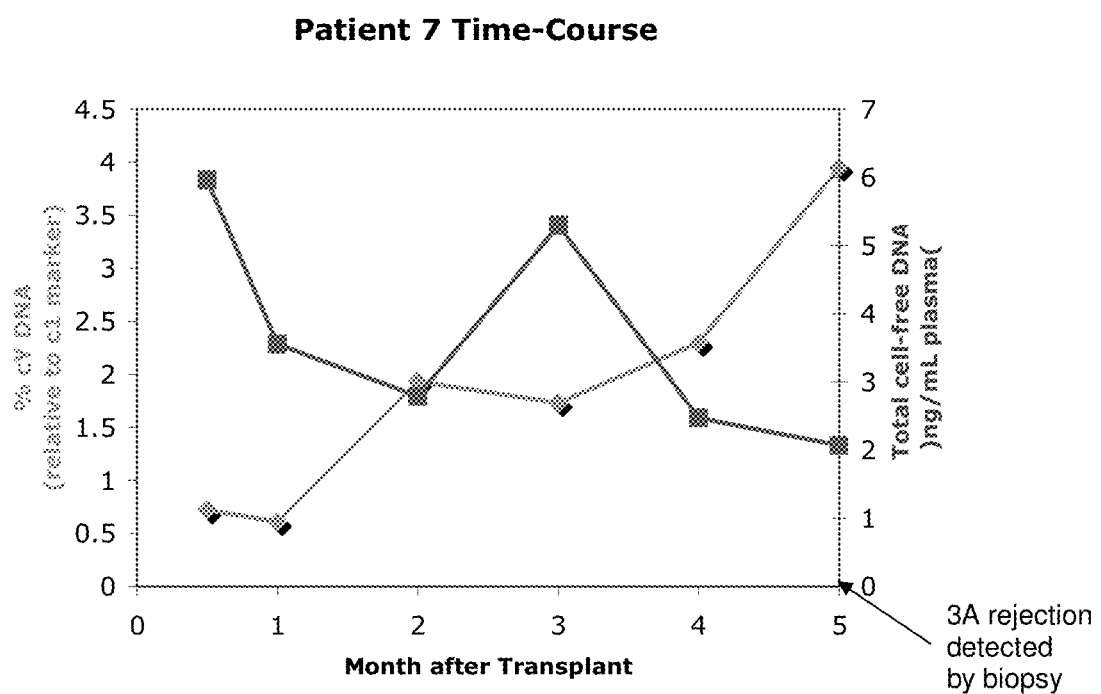
FIG. 4 shows a time course study for detection of donor DNA in a transplant patient that received a gender mismatched transplant and suffered a 3A rejection episode.

Levels of chromosome Y in plasma were monitored at several time points following transplantation for some of these patients, and compared with biopsy time points for organ rejection. For patient 6, a 3A grade rejection was detected after biopsy 21 months after transplant. The level of chromosome Y detected in plasma was neglible in plasma at three months prior to rejection, but increased >10-fold to 2% of total genomic fraction at the time a biopsy determined rejection. The highest levels of cY in the plasma DNA are seen at this time (FIG. 3). The results in FIG. 3 suggest that the overall levels of cell-free DNA in the plasma are not diagnostic of organ failure and do not track the "donor-specific" DNA signal Similar trends were observed for another patient that had cY levels increasing at 5 months after transplant when a biopsy detected a grade 3A rejection (FIG. 4). The percentage of cY (or % "Donor") DNA is increasing before and highest at rejection time. Like above, the amount of total cell-free DNA does not seem diagnostic for heart rejection Collectively, these results establish that for heart transplant patients, donor-derived DNA present in plasma can serve as a potential marker for the onset of organ failure.

Example 2: Genotyping of Transplant Donor and Transplant Recipient

FIG. 5 shows a general strategy to monitor all transplant patients. Genotyping of donor and recipient can establish a single nucleotide polymorphism (SNP) profile for detecting donor DNA. Shotgun sequencing of cell-free DNA in plasma, with analysis of observed unique SNPs, allows quantitation of % Donor DNA in the sample. While any single SNP may be difficult to detect with so little DNA in plasma, with hundred of thousands or more signals to consider, high sensitivity should be possible Libraries of mixed genotypes can be created using two CEU (Mormon, Utah) HapMap lines. Approximately 1.2 million total variations between these two individuals were already established using existing genotyping platforms (e.g., Illumina Golden Gate). Usable SNPs must be homozygous for the recipient and ideally homozygous for the donor as well. Usable SNPs comprise: (i) approximately 500,000 heterozygous donor SNPs (count will be ½ of total donor fraction), (ii) approximately 160,000 homozygous donor SNPs.

Figures 6A, 6B:
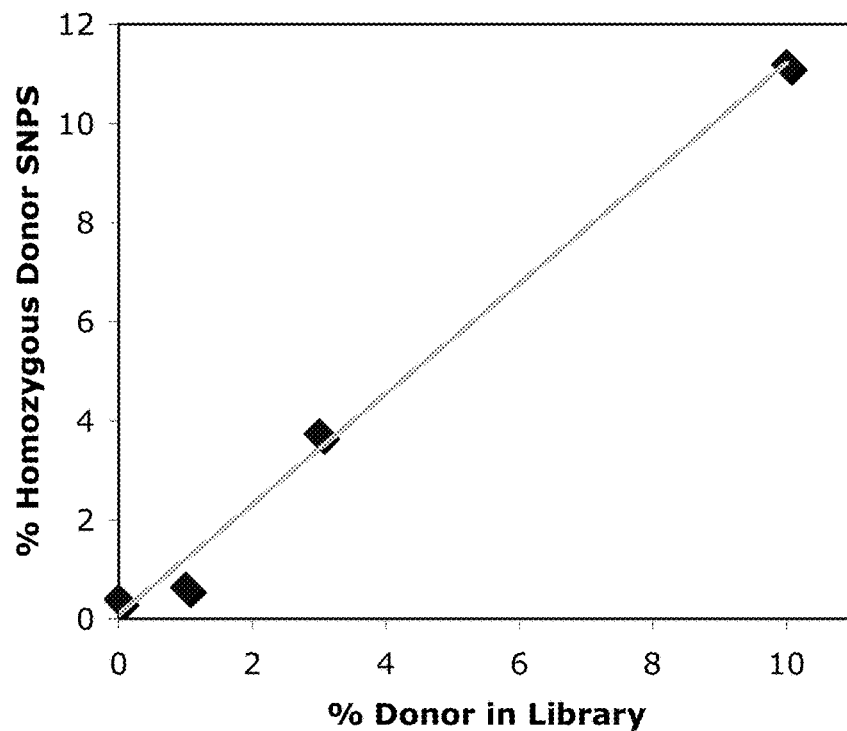
FIG. 6A-6B shows sequencing results comparing four levels of substitutions of donor DNA into recipient DNA.

Sequencing Results: 4 lanes of Illumina sequencing are used to compare 4 different levels of substitution of Donor DNA into Recipient DNA (See FIG. 6). Error rate of sequencing is currently ~0.3-0.5% for base substitution. The use of quality scores for improved filtering of SNP calls, or the use of resequencing, should reduce error rate and increase sensitivity. The use of more SNP locations (from full genotyping) should also improve yield of signal with no change in protocol.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A nucleic acid sequencing apparatus for monitoring status of a transplant in a transplant recipient by quantifying transplant-derived cell-free nucleic acids in a biological sample obtained from said transplant recipient, wherein the transplant-derived cell-free nucleic acids make up between 0.03% to 8.0% of total cell free nucleic acids in said biological sample, said nucleic acid sequencing apparatus comprising (a) a high-throughput sequencing device, and (b) a computing device that comprises a computer executable logic that is recorded on a computer readable medium causing a processor to perform a set of instructions to:

i. receive at least 1000 nucleic acid sequence reads from said high-throughput sequencing device, wherein said at least 1000 nucleic acid sequence reads are obtained from cell-free nucleic acids from said biological sample, ii. determine a base call error rate for said at least 1000 nucleic acid sequence reads;

iii. identify nucleic acid sequence reads with a base call error rate below 0.5% of said at least 1000 nucleic acid sequence reads thereby providing identified nucleic acid sequence reads with a base call error rate below 0.5% and increasing sensitivity of distinguishing nucleic acids between said transplant and said transplant recipient;

iv determine at least 100 single nucleotide polymorphisms that are distinguishable between said transplant recipient and said transplant from said identified nucleic acid sequence reads with a base call error rate below 0.5%, wherein said at least 100 single nucleotide polymorphisms that are distinguishable between said transplant recipient and said transplant from said identified nucleic acid sequence reads with a base call error rate below 0.5% are selected from the group consisting of heterozygous single nucleotide polymorphisms, homozygous single nucleotide polymorphisms, and both heterozygous and homozygous single nucleotide polymorphisms; and v. provide a quantified amount of transplant-derived cell-free nucleic acids in said biological sample based on the determination of said at least 100 single nucleotide polymorphisms that are distinguishable between said transplant recipient and said transplant from said identified nucleic acid sequence reads with a base call error rate below 0.5%, wherein said transplant derived cell-free nucleic acids in said biological sample make up between about 0.03% to 8.0% of said total cell-free nucleic acids in said biological sample.

2. The nucleic acid sequencing apparatus of claim 1, wherein said cell-free nucleic acids comprise DNA.

3. The nucleic acid sequencing apparatus of claim 1, wherein said transplant-derived cell-free nucleic acids are DNA.

4. The nucleic acid sequencing apparatus of claim 1, wherein said transplant recipient is a solid organ transplant recipient.

5. The nucleic acid sequencing apparatus of claim 1, wherein said computing device that comprises said computer executable logic recorded on said computer readable medium causes a processor to perform a set of instructions to determine at least 400 single nucleotide polymorphisms that are distinguishable between said transplant recipient and said transplant from said identified nucleic acid sequence reads with a base call error rate below 0.5%.

6. The nucleic acid sequencing apparatus of claim 1, wherein said computing device that comprises said computer executable logic recorded on said computer readable medium causes a processor to perform a set of instructions to determine at least 1,000 single nucleotide polymorphisms that are distinguishable between said transplant recipient and said transplant from said identified nucleic acid sequence reads with a base call error rate below 0.5%.

7. The nucleic acid sequencing apparatus of claim 1, wherein said computing device that comprises said computer executable logic recorded on said computer readable medium causes a processor to perform a set of instructions to determine at least 5,000 single nucleotide polymorphisms that are distinguishable between said transplant recipient and said transplant from said identified nucleic acid sequence reads with a base call error rate below 0.5%.

8. The nucleic acid sequencing apparatus of claim 1, wherein said single nucleotide polymorphisms that are distinguishable between said transplant recipient and said transplant comprise homozygous single nucleotide polymorphisms.

9. The nucleic acid sequencing apparatus of claim 1, wherein said single nucleotide polymorphisms that are distinguishable between said transplant recipient and said transplant comprise heterozygous single nucleotide polymorphisms.

10. The nucleic acid sequencing apparatus of claim 1, wherein said single nucleotide polymorphisms that are distinguishable between said transplant recipient and said transplant comprise homozygous single nucleotide polymorphisms and heterozygous single nucleotide polymorphisms.

11. The nucleic acid sequencing apparatus of claim 1, wherein said biological sample is a urine sample.

12. The nucleic acid sequencing apparatus of claim 1, wherein said biological sample is a sample selected from the group consisting of a blood sample, a plasma sample, and a serum sample.

13. The nucleic acid sequencing apparatus of claim 1, wherein said biological sample is a plasma sample.

14. The nucleic acid sequencing apparatus of claim 1, wherein said high-throughput sequencing device is a sequencing-by-synthesis high throughput sequencing device.

15. The nucleic acid sequencing apparatus of claim 1, wherein said nucleic acid sequence reads comprise sequence reads with lengths at least about 36 base pairs.

16. The nucleic acid sequencing apparatus of claim 4, wherein said solid organ transplant recipient has received a solid organ transplant from the list consisting of a kidney transplant, a lung transplant, a heart transplant, a liver transplant, a pancreas transplant, a skin transplant, and combinations thereof.

17. The nucleic acid sequencing apparatus of claim 4, wherein said solid organ transplant recipient has received a kidney transplant.

18. The nucleic acid sequencing apparatus of claim 1, wherein said base call error rate is a base substitution error rate.

19. The nucleic acid sequencing apparatus of claim 1, wherein said computing device that comprises said computer executable logic recorded on said computer readable medium causes a processor to perform a set of instructions to determine a base call error rate for each read of said at least 1000 nucleic acid sequence reads.

* * * * *